(12) United States Patent
Johnson, Jr. et al.

(10) Patent No.: US 7,691,392 B2
(45) Date of Patent: Apr. 6, 2010

(54) METHOD OF TREATING MULTIPLE MYELOMA USING 17-AAG OR 17-AG OR A PRODRUG OF EITHER

(75) Inventors: Robert G. Johnson, Jr., Lafayette, CA (US); Alison L. Hannah, Sebastopol, CA (US); Gillian F. Cropp, San Francisco, CA (US); Yiqing Zhou, Lafayette, CA (US); J. Michael Sherrill, Danville, CA (US)

(73) Assignee: Kosan Biosciences Incorporated, Princeton, NJ (US)

( * ) Notice: Subject to any disclaimer, the term of this patent is extended or adjusted under 35 U.S.C. 154(b) by 257 days.

(21) Appl. No.: 11/412,298

(22) Filed: Apr. 26, 2006

(65) Prior Publication Data

US 2006/0252739 A1 Nov. 9, 2006

Related U.S. Application Data

(60) Provisional application No. 60/676,449, filed on Apr. 29, 2005, provisional application No. 60/680,944, filed on May 12, 2005, provisional application No. 60/721,707, filed on Sep. 28, 2005, provisional application No. 60/749,200, filed on Dec. 9, 2005.

(51) Int. Cl.
  *A61K 31/395* (2006.01)
(52) U.S. Cl. .............. 424/234.1; 424/93.71; 424/143.1; 424/184.1; 424/193.1; 424/244.1; 514/252.13
(58) Field of Classification Search .............. 424/93.71, 424/143.1, 184.1, 193.1, 400, 623; 514/183, 514/252.13
See application file for complete search history.

(56) References Cited

U.S. PATENT DOCUMENTS

| 4,261,989 | A | 4/1981 | Sasaki |
|---|---|---|---|
| 5,387,584 | A | 2/1995 | Schnur |
| 5,415,869 | A | 5/1995 | Straubinger |
| 5,424,073 | A | 6/1995 | Rahman |
| 5,510,118 | A | 4/1996 | Bosch |
| 5,534,270 | A | 7/1996 | De Castro |
| 5,662,883 | A | 9/1997 | Bagchi |
| 5,683,715 | A | 11/1997 | Boni |
| 5,932,566 | A | 8/1999 | Schnur |
| 6,682,758 | B1 | 1/2004 | Tabibi |
| 2004/0022869 | A1* | 2/2004 | Chen et al. .................. 424/623 |
| 2004/0058021 | A1 | 3/2004 | Aggarwal |
| 2005/0043233 | A1 | 2/2005 | Stefanic |
| 2005/0227955 | A1 | 10/2005 | Adams |
| 2005/0256097 | A1 | 11/2005 | Zhong |
| 2006/0067953 | A1 | 3/2006 | Mansfield |
| 2006/0239909 | A1 | 10/2006 | Anderson |

FOREIGN PATENT DOCUMENTS

| WO | WO 98/30205 A1 | 7/1998 |
|---|---|---|
| WO | WO 00/71163 A1 | 11/2000 |
| WO | WO 01/10412 A1 | 2/2001 |
| WO | WO 03/086381 A1 | 10/2003 |
| WO | WO 2004/082676 A1 | 9/2004 |
| WO | WO 2005/115431 A2 | 12/2005 |
| WO | WO 2006/034147 A2 | 3/2006 |
| WO | WO 2006/094029 A2 | 9/2006 |

OTHER PUBLICATIONS

Hideshima et al., "Molecular Mechanisms of Novel Therapeutic Approaches for Multiple Myeloma." Nature Reviews 2002:2;927-937.*
Dai et al., "Combined treatment with the checkpoint abrogator UCN-01 and MEK1/2 inhibitors potently induces apoptosis in drug-sensitive and -resistant myeloma cells through an IL-6—independent mechanism." Blood 2002:100(9);3333-3343.*
Bagatell et al. (2001) *Clin. Cancer. Res.* 7:2076-2084, "Destabilization of Steroid Receptors by Heat Shock Protein 90-binding Drugs: A Ligand-independent Approach to Hormonal Therapy of Breast Cancer".
Banerji et al. (2002) *Proc. 93rd Annu. Meet. Am. Assoc. Cancer Res.* Abstract 1352, "A pharmacokineticaly (PK)-pharmacodynamically (PD) driven Phase I trial of the HSP90 molecular chaperone inhibitor 17-allylamino-17-demethoxygeldanamycin (17AAG)".
Banerji et al. (2005) *J. Clin. Oncol.* 23(1):4152-4161, "Phase I Pharmacokinetic and Pharmacodynamic Study of 17-Allylamino-17-Demethoxygeldanamycin in Patients with Advanced Malignancies".
Bladé et al. (1998) *Br. J Haematol.* 102(5):1115-23, "Criteria for Evaluating Disease Response and Progression in Patients with Multiple Myeloma Treated by High-dose Therapy and Haemopoietic Stem Cell Transplantation".
Burger et al. (2004) *Anti-Cancer Drugs* 15 (4):377-387, "17-(Allylamino)-17-demethoxygeldanamycin activity in human melanoma models" (abstract).
Chanan-Khan et al. (2005), *Proc. Am. Soc. Hematology* 105:11, abst. 362, "Phase 1 Clinical Trial of KOS-953 + Bortozomib (BZ) in Relapsed Refractory Multiple Myeloma (MM)".
Chanan-Khan et al. (2005), *Proc. Eur. Hematology Assoc., 10th Congress*, Abst. 0632, KOS-953 (a Heat Shock Protein 90 Inhibitor) as Single Agent or in Combination with Bortezomib in Patients with Relapsed Refractory Multiple Myeloma.
Chanan-Khan et al., *42nd ASCO Ann. Mtg.*, Atlanta, GA, Jun. 2-5, 2006, Poster 3066, "Phase I Clinical Trial of KOS -953 + Bortezomib (BZ) in Refractory Multiple Myeloma (MM)".
Chanan-Khan et al., *Proc. 41st ASCO Ann. Mtg.* May 13-17 2005, Orlando, FL, abstract 6682, "Dose Escalating Trial of 17-AAG with bortezomib (BZ) in Patients with Refractory Multiple Myeloma".

(Continued)

*Primary Examiner*—Frederick Krass
*Assistant Examiner*—Walter E Webb
(74) *Attorney, Agent, or Firm*—Elliott Korsen; Fox Rothschild LLP

(57) ABSTRACT

A method for treating multiple myeloma in a subject by administering 17-allylamino-17-demethoxy-geldanamycin or 17-amino geldanamycin, or a prodrug of either 17-AAG or 17-AG, to the subject.

38 Claims, 6 Drawing Sheets

OTHER PUBLICATIONS

Chen et al. (2005) *Cancer Chemother. Pharmacol.* 55:237-243, "Population pharmacokinetic analysis of 17-(allylamino)-17-demethoxygeldanamycin (17AAG) in adult patients with advanced malignancies" (abstract).

Davies et al. (2003) *Blood.* 102(13):4504-11, "Insights into the multistep transformation of MGUS to myeloma using microarray expression analysis".

Egorin et al. (1998) *Cancer Res.* 58:2385-2396, "Metabolism of 17-(allylamino)-17-demethoxygeldanamycin (NSC 330507) by murine and human hepatic preparations".

Goetz et al. (2005) *J. Clin. Oncol.* 23(6):1078-1087, "Phase I trial of 17-allylamino-17-demethoxygeldanamycin in patients with advanced cancer" (abstract).

Grem et al. (2005), *J. Clin. Oncol.* 23(9):1885-93, "Phase I and pharmacologic study of 17-(allylamino)-17-demethoxygeldanamycin in adult patients with solid tumors".

Hostein et al. (2001) *Cancer Res.* 61:4003-4009, "Inhibition of Signal Transduction by the Hsp90 Inhibitor 17-Allylamino-17-demethoxygeldanamycin Results in Cytostasis and Apoptosis".

Jiang and Shapiro. (2002) *Proc. 93rd Ann. Meet. Am Assoc. Cancer Res.* Abstract 1645, "17-AAG induces Rb-dependent G1 arrest in lung cancer cell lines".

Mitsiades et al. (2002) *Oncogene* 21, 5673-83, "Activation of NF-kappaB and upregulation of intracellular anti-apoptotic proteins via the IGF-1/Akt signaling in human multiple myeloma cells: therapeutic implications" (abstract).

Mitsiades et al. (2004), *Proc. Am. Soc. Hematology* 104:11, Abst 2404, "Anti-Tumor Activity of KOS-953, a Cremophor Based Formulation of the hsp90 inhibitor 17-AAG".

Mitsiades et al. (2006) *Blood* 107 (3), 1092-1100, "Antimyeloma activity of heat shock protein-90 inhibition".

Mitsiades et al., *41st ASCO Ann. Mtg.*, Orlando, FL, May 13-17, 2005, Poster 3056, "Phase I Trial of 17-AAG in Patients with Relapsed Refractory Multiple Myeloma".

Modi et al., *42nd ASCO Ann. Mtg.*, Atlanta, GA, Jun. 2-5, 2006, 26:501, "Phase I Dose Escalating Trial of KOS-953, a Heat Shock Protein 90 Inhibitor, and Trastuzumab" (slide presentation).

Modi et al., *Proc. AACR Washington DC 2006*, 47:2919, "Phase I Dose Escalating Trial of KOS-953 (Heat Shock Protein 90 Inhibitor) and Trastuzumab (T)".

Munster et al. (2001) *Proc. Am. Soc. Clin. Oncol.* 20:Abstract 327, "Phase I Trial of 17-(allylamino)-17-Demethoxygeldanamycin (17-AAG) in Patients (Pts) with Advanced Solid Malignancies".

National Cancer Institute (2003) Common Terminology Criteria for Adverse Events v3.0 (CTCAE).

Nguyen et al. (2000) *Ann. Thorac. Surg.* 70:1853-1860, "Modulation of metastasis phenotypes of non-small cell lung cancer cells by 17-allylamino 17-demethoxy geldanamycin" (abstract).

Nimmanapalli et al. (2001) *Cancer Res.* 61:1799-1804, "Geldanamycin and Its Analogue 17-Allylamino-17-demethoxygeldanamycin Lowers Bcr-Abl Levels and Induces Apoptosis and Differentiation of Bcr-Abl-positive Human Leukemic Blasts".

Richardson et al. (2005), *Proc. Am. Soc. Hematology* 105:11, Abst. 361, "Safety and Activity of KOS-953 in Patients with Relapsed Refractory Multiple Myeloma (MM): Interim Results of a Phase 1 Trial."

Sasaki et al. (1979), *J. Antibiotics* 32 (8), 849-851, "Growth inhibition of virus transformed cells in vitro and antitumor activity in vivo of geldanamycin and its derivatives".

Schulte and Neckers. (1998) *Cancer Chemother. Pharmacol.* 42:273-279, "The benzoquinone ansamycin 17-allylamino-17-demethoxygeldanamycin binds to HSP90 and shares important biologic activities with geldanamycin" (abstract).

Wermuth (2003), "Designing Prodrugs and Bioprecursors," in Wermuth, ed., *The Practice of Medicinal Chemistry*, 2nd Ed., pp. 561-586 (Academic Press 2003).

Anderson, Eur. J. Cancer Supp. 1 (5), S6 (2003), "Targeting host-tumour interactions in myeloma therapies".

Kasdan et al., J. Clin. Oncol., 2005 ASCO Ann. Mtg. Proc., 23 (16S), Part I/II (Jun. 1 Supp.), 2005:9609, "Combination of the mTOR inhibitor rapamycin and 17-allylamino-17-demethoxygeldanamycin [17-AAG] inhibits proliferation and induces apoptosis in multiple myeloma (MM)".

Mimnaugh et al., *Mol. Cancer Res.* 2006, 4 (9), 667-681, "Endoplasmic Reticulum Vacuolization and Valosin-Containing Protein Relocalization Result from Simultaneous Hsp90 Inhibition by Geldanamycin and Proteasome Inhibition by Velcade".

Mimnaugh et al., *Molecular Cancer Therapeutics* 2004, 3 (5), 551-566, "Simultaneous inhibition of hsp90 and the proteasome promotes protein ubiquitination, causes endoplasmic reticulum-derived cytosolic vacuolization, and enhances antitumor activity".

Mimnaugh et al., *Proc. Am. Assn. Cancer Res.* 2003, 44 (2nd), 153, Abst. R785, "Geldanamycin combined with PS-341 synergistically activates a cellular stress response, causes massive accumulation of ubiquitinated proteins and shows enhanced antitumor activity".

Richardson et al., Blood (ASH Ann. Mtg. Abstracts) 2006, 108: Abst 406, "A Multicenter Phase I Clinical Trial of Tanespimycin (KOS-953) + Bortezomib (BZ): Encouraging Activity and Manageable Toxicity in Heavily Pre-treated Patients with Relapsed Refractory Multiple Myeloma (MM)".

Semenov et al., Leukemia Research 26, 271-280 (2002), "Growth inhibition and apoptosis of myeloma cells by the CDK inhibitor flavopiridol".

Cleveland Clinic Multiple Myeloma Research Center, Multiple Myeloma and Plasma Cell Dyscrasia, http://my.clevelandclinic.org/myeloma/education/multiple_myeloma.aspx (last visited Jan. 26, 2009).

Richard Ravel, Clinical Laboratory Medicine, Mosby, 350, (6th ed. 1995).

Pisters et al., Amino Acid Metabolism in Human Cancer Cachexia, 10, pp. 107-132, Annu. Rev. Nut. (1990).

Dols et al, Specific Alterations in the Serum Amino Acid Profile of Patients with Lung Cancer and Head and Neck Cancer, Oncologia, 29(7), 283-290, pp. 17-24, 3 (2006).

MacDonald et al, Understanding and Managing Cancer Cachexia, J Am Coll Surg, 197(1), pp. 143-159, p. 144, (2003).

George et al., "Cotreatment with 17-Allylamino-Demethoxygeldanamycin and FLT-3 Kinase Inhibitor PKC412 is Highly Effective against Human Acute Myelogenous Leukemia Cells with Mutant FLT-3," Cancer Research (May 15, 2004); vol. 64, pp. 3645-3652.

Australian International Search Report issued for application No. SG 2007 17279-4.

* cited by examiner

Dose level 340 mg/m², (mean, SD)

AUC$_{total}$17-AAG and AUC$_{total}$17-AG for all patients

| AUC 17-AAG f(x)=7.20E+1*x+−5.91E+3  R2=7.55E−1 | AUC 17-AG f(x)=4.48E+1*x+−3.27E+3  R2=3.58E−1 |

$C_{max}$ Day 1 and Day 11 (Banerji, et al.) vs. data from this study (Example 2)

$AUC_{total}$ for six dose levels in Banerji et al. (2002) compared to Example 2

Increased apoptosis as measured by the mitochondrial potential in plasma cells (p=0.06)

BM, AKT in total cells (p=0.057)

Percent change in serum M-spike and urine M-protein of a patient (150 mg/m² dose level)

|  | Baseline | Post Cycle 1 | Post Cycle 2 | Post Cycle 3 | End of Study |
|---|---|---|---|---|---|
| M-Spike (mg/dL) | 1770 | ND | 1190 | 1290 | 2240 |
| Urine M-Protein (mg/24h) | 317 | 245 | 187 | ND | 1598 |

Percent change in serum M-spike and total IgG of a patient (275 mg/m² dose level)

|  | Baseline | Post C1 | Post C2 | Post C3 | Post C4 | Post C5 | Post C6 | Post C7 | End Study |
|---|---|---|---|---|---|---|---|---|---|
| M-Spike (g/dL) | 2.45 | 2.24 | 2.51 | 2.38 | 2.18 | 2.24 | 2.25 | 2.24 | 2.18 |
| Total Ig G (mg/dl) | 3040 | 2470 | 2830 | 2770 | 2930 | 2520 | 2680 | 2520 | 2680 |

METHOD OF TREATING MULTIPLE MYELOMA USING 17-AAG OR 17-AG OR A PRODRUG OF EITHER

CROSS-REFERENCE TO RELATED APPLICATIONS

This application claims the benefit under 35 U.S.C. §19(e) of U.S. Provisional Applications Nos. 60/676,449, filed Apr. 29, 2005; 60/680,944, filed May 12, 2005; 60/721,707, filed Sep. 28, 2005; and 60/749,200, filed Dec. 9, 2005; the disclosures of which are incorporated herein by reference.

BACKGROUND OF THE INVENTION

1. Field of the Invention

This invention relates to a method of treating multiple myeloma using 17-allylamino-17-demethoxygeldanamycin or 17-aminogeldanamycin, or a prodrug of either.

2. Description of Related Art

Multiple myeloma ("MM", also known as myeloma or plasma cell myeloma) is an incurable but treatable cancer of the plasma cell. Plasma cells are an important part of the immune system, producing immunoglobulins (antibodies) that help fight infection and disease. MM is characterized by excessive numbers of abnormal plasma cells in the bone marrow ("BM") and overproduction of intact monoclonal immunoglobulins (IgG, IgA, IgD, or IgE; "M-proteins") or Bence-Jones protein (free monoclonal light chains). Hypercalcemia, anemia, renal damage, increased susceptibility to bacterial infection, and impaired production of normal immunoglobulin are common clinical manifestations of MM. MM is often also characterized by diffuse osteoporosis, usually in the pelvis, spine, ribs, and skull.

Therapies for MM include chemotherapy, stem cell transplantation, high-dose chemotherapy with stem cell transplantation, and salvage therapy. Chemotherapies include treatment with Thalomid® (thalidomide), Velcade® (Bortezomib), Aredia® (pamidronate), steroids, and Zometa® (zoledronic acid). However many chemotherapy drugs are toxic to actively dividing non-cancerous cells, such as cells of the BM, the lining of the stomach and intestines, and the hair follicles. Therefore, chemotherapy may result in a decrease in blood cell counts, nausea, vomiting, diarrhea, and loss of hair.

Conventional chemotherapy, or standard-dose chemotherapy, is typically the primary or initial treatment for patients with MM. Patients also may receive receive chemotherapy in preparation for high-dose chemotherapy and stem cell transplant. Induction therapy (conventional chemotherapy prior to a stem cell transplant) can be used to reduce the tumor burden prior to transplant. Certain chemotherapy drugs are more suitable for induction therapy than others, because they are less toxic to BM cells and result in a greater yield of stem cells from the BM. Examples of chemotherapy drugs suitable for induction therapy include dexamethasone, thalidomide/dexamethasone, VAD (vincristine, Adriamycin® (doxorubicin), and dexamethasone in combination), and DVd (pegylated liposomal doxorubicin (Doxil®, Caelyx®), vincristine, and reduced schedule dexamethasone in combination).

The standard treatment for MM is melphalan in combination with prednisone (a corticosteroid drug), achieving a response rate of 50%. Unfortunately, melphalan is an alkylating agent and is less suitable for induction therapy. Corticosteroids (especially dexa-methasome) are sometimes used alone as MM therapy, especially in older patients and those who cannot tolerate chemotherapy. Dexamethasone is also used as a form of induction therapy, alone or in combination with other agents. VAD is the most commonly used induction therapy, but DVd has recently been shown to be effective as induction therapy. Bortezomib has been approved recently for the treatment of MM, but it is very toxic. However, none of the existing therapies offer a significant potential for a cure.

17-Allylamino-17-demethoxygeldanamycin ("17-AAG", also sometimes referred to as 17-allylaminogeldanamycin) is a semi-synthetic analog of the naturally occurring compound geldanamycin (Sasaki et al., 1981). Geldanamycin is obtainable by culturing a producing organism, such as *Streptomyces hygroscopicus* var. *geldanus* NRRL 3602. Another biologically active geldanamycin derivative is 17-aminogeldanamycin ("17-AG"), which is produced in the human body by metabolism of 17-AAG. 17-AG can also be made from geldanamycin (Sasaki et al. 1979). While geldanamycin and its analogs have been studied intensively as anti-cancer agents in the 1990s (e.g., Sasaki et al., 1981; Schnur, 1995; Schnur et al., 1999), none of them has been approved for anti-cancer use.

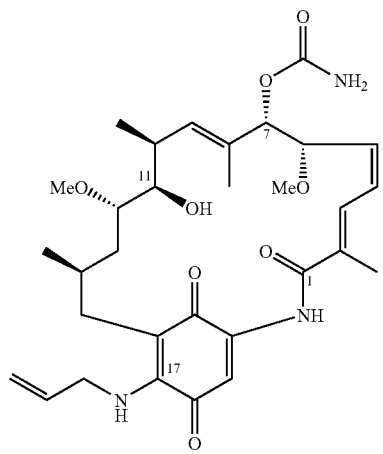

17-AAG

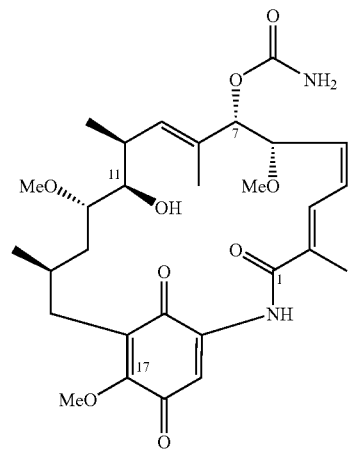

Geldanamycin

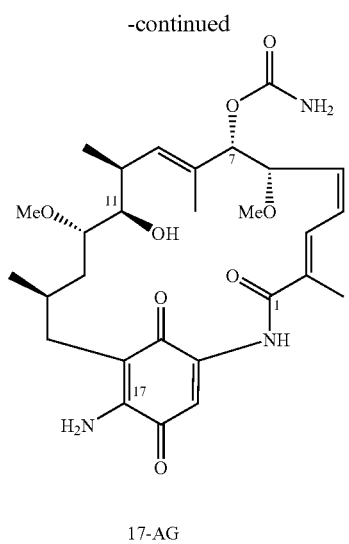

17-AG

17-AAG and geldanamycin are believed to act by binding to and inhibiting the activity of heat shock protein-90 ("Hsp90") (Schulte and Neckers, 1998). Hsp90 acts as a chaperone for the normal processing of many cellular proteins ("client proteins") and is found in all mammalian cells. Stress (hypoxia, heat, etc.) induces a several-fold increase in its expression. There exist other stress induced proteins, such as heat shock protein-70 ("Hsp70"), which also play a role in cellular response to and recovery from stress.

In cancer cells, Hsp90 inhibition leads to disruption of the interaction between Hsp90 and its client proteins, such as erbB2, steroid receptors, raf-1, cdk4, and Akt. For example, exposure to 17-AAG results in depletion of erbB2 and destabilization of Raf-1 and mutant p53 in SKBr3 breast cancer cells (Schulte and Neckers, 1998), depletion of steroid receptors in breast cancer cells (Bagatell et al., 2001), depletion of Hsp90 and down-regulation of Raf-1 and erbB2 in MEXF 276 L melanoma cells (Burger et al., 2004), depletion of Raf-1, c-Akt, and Erk1/2 in colon adenocarcinoma cells (Hostein et al., 2001), down-regulation of intracellular Bcr-Abl and c-Raf proteins and reduction of Akt kinase activity in leukemia cells (Nimmanapalli et al., 2001), degradation of cdk4, cdk6, and cyclin E in lung cancer cells with wild-type Rb (Jiang and Shapiro, 2002), and depletion of erbB 1 (EGFR) and erbB2 (p185) levels in NSCLC cells (Nguyen et al., 2000).

Because of the activity of 17-AAG relative to Hsp90 and other proteins involved in oncogenesis and metastasis of cancer cells, a number of clinical investigators have evaluated its effectiveness as an anti-cancer agent in human clinical trials. From these various trials, the Cancer Therapy Evaluation Program (CTEP) of the National Cancer Institute recommended these Phase 2 dose/schedule regimens for further study: 220 mg/m² (mg per square meter of body surface area of the patient or subject) administered twice weekly for 2 out of 3 weeks, 450 mg/m² administered once a week continuously or with a rest or break, and 300 mg/m² once a week for 3 weeks out of 4 weeks. Results of various clinical trials— almost exclusively with patients having solid tumors—with 17-AAG generally showed limited clinical activity and are summarized below:

(a) A Phase 1 trial in adult patients with solid tumors was conducted in which patients received 17-AAG daily for 5 days every 3 weeks. The starting dose was 10 mg/m² and was escalated to 56 mg/m², with a maximum tolerated dose ("MTD") and recommended Phase 2 dose defined as 40 mg/m². The protocol was amended to exclude patients with significant pre-existing liver disease, after which patients were treated at doses up to 110 mg/m² on the same schedule. No objective tumor responses were observed. Due to dose limiting reversible hepatotoxicity, the protocol was further amended to dose patients on a twice weekly schedule every other week starting at a dose of 40 mg/m² per day. At daily doses of 40 and 56 mg/m² for 5 days, the peak plasma concentrations were 1,860±660 and 3,170±1,310 nM, respectively. For patients treated at 56 mg/m² average AUC values for 17-AAG and 17-AG were 6,708 and 5,558 nM*h, respectively, and average $t_{1/2}$ 3.8 and 8.6 hours, respectively. Clearances of 17-AAG and 17-AG were 19.9 and 30.8 L/h/m², respectively, and $V_z$ values were 93 and 203 L/m², respectively (Grem et al., 2005).

(b) In a second Phase 1 trial, patients with advanced solid tumors received 17-AAG on a daily×5 schedule at a starting dose of 5 mg/m². At the 80 mg/m², dose limiting toxicities (hepatitis, abdominal pain, nausea, dyspnea) were observed but dose escalations nevertheless were continued until the dose reached 157 mg/m²/day. Further dose schedule modifications were implemented to allow twice weekly dosing. At the 80 mg/m² dose level, the $t_{1/2}$ was 1.5 hours and the plasma $C_{max}$ was 2,700 nM. Similarly, for 17-AG the $t_{1/2}$ was 1.75 hours and the $C_{max}$ was 607 nM. Plasma concentrations exceeded those needed to achieve cell kill (10-500 nM) in in vitro and in vivo xenograft models (Munster et al., 2001).

(c) A Phase 1 trial of 17-AAG was conducted in which patients with advanced solid tumors were treated weekly for 3 out of every 4 weeks at a starting dose of 10 mg/m², with a recommended Phase 2 dose of 295 mg/m². Dose escalations reached a dose of 395 mg/m², at which nausea and vomiting secondary to pancreatitis and grade 3 fatigue were observed. The dosing schedule was amended to allow dosing twice weekly for 3 out of every 4 weeks and twice weekly for 2 out of every 3 weeks. A population pharmacokinetic (PK) analysis was performed on data obtained from this trial. The Vd (volume of distribution) for 17-AAG was 24.2 L for the central compartment and 89.6 L for the peripheral compartment. Clearance values were 26.7 L/h and 21.3 L/h for 17-AAG and 17-AG, respectively. Metabolic clearance indicated that 46.4% of 17-AAG was metabolized to 17-AG. No objective tumor responses have been observed in this trial to date. (Chen et al., 2005).

(d) Another Phase 1 trial in patients with solid tumors and lymphomas was conducted using a weekly dosing for 3 weeks out of a 4 week cycle. The starting dose was 15 mg/m². Dose escalation reached 112 mg/m² without significant toxicity and were continued with an objective of reaching a dose range of "biological" activity. The MTD for weekly 17-AAG was reached at 308 mg/m². No objective tumor responses have been observed to date in this trial, and the levels of Hsp90 client proteins measured were unchanged during therapy. No correlation between chaperone or client protein levels and 17-AAG or 17-AG PK was seen. There was also no correlation between the 17-AAG PK and its clinical toxicity (Goetz et al., 2005).

(e) Another Phase 1 trial was conducted using a once weekly administration schedule, including 11 patients with metastatic melanoma. The starting dose was 10 mg/m², and dose limiting toxicity was observed at 450 mg/m²/week (grade ¾ elevation of AST). At higher doses (16-450 mg/m²/week) the 17-AAG formulation employed contained 10-40 mL dimethylsulfoxide (DMSO) in a single infusion, which likely contributed to the gastrointestinal toxicity that was observed in the trial. Among the patients treated at 320-450 mg/m$^2$, two showed radiologically documented long term stable disease. No complete or partial responses were recorded. At the highest dose level (450 mg/m$^2$) the plasma 17-AAG concentrations exceeded 10 μM and remained above 120 nM for periods in excess of 24 hours. At the highest dose level of 450 mg/m$^2$, the mean volume of distribution was 142.6 L, mean clearance was 32.2 L/h, and the mean peak plasma level was 8,998 μg/L. There was a linear correlation between dose and area under the curve (AUC) for the dose levels studied. Pharmacodynamic (PD) parameters were also measured and induction of the co-chaperone protein Hsp70 was observed in 8 of 9 patients treated at 320-450 mg/m$^2$/week. Depletion of client proteins was also observed in tumor biopsies: CDK4 in 8 out of 9 patients and Raf-1 depletion in 4 out of 6 patients at 24 hours. These data indicated that Hsp90 in tumors is inhibited for between 1 and 5 days. (Banerji et al., 2005).

The in vivo anti-MM activity of 17-AAG has been studied using a model of diffuse GFP positive MM lesions in SCID/NOD mice (Mitsiades et al., 2006). Survival analysis showed that treatment significantly prolonged median overall survival, but non-clinical data are frequently not predictive of clinical activity. As discussed above, this has particularly been the case for 17-AAG in solid tumors, where the promise of pre-clinical data has not been borne out in Phase 1 clinical trials.

Thus, despite intensive efforts to develop 17-AAG as an anti-cancer agent, no regulatory agency has approved it for the treatment of any cancer. There remains a need for methods of dosing and administering 17-AAG and prodrugs of 17-AAG (and its metabolic counterpart 17-AG) so that its potential therapeutic benefits can be realized. The present invention provides such methods that are efficacious in the treatment of MM using 17-AAG.

A list references cited herein is provided at the end of this specification. All documents cited herein are incorporated herein by reference as if each such publication or document were specifically and individually incorporated herein by reference.

BRIEF SUMMARY OF THE INVENTION

The present invention provides methods for treating multiple myeloma in a subject in need of such treatment, comprising the step of administering a pharmaceutical formulation to said subject, wherein said pharmaceutical formulation comprises a therapeutically effective dose of 17-AAG or 17-AG or a prodrug of either 17-AAG or 17-AG and optionally a pharmaceutically acceptable carrier or diluent, and optionally repeating said step until no further therapeutic benefit is obtained.

In one embodiment, the method comprises the administration of multiple doses of 17-AAG or a prodrug thereof to a subject with MM over a time period of at least 2 weeks, wherein each such dose is in the range of about 275 mg/m$^2$ to about 420 mg/m$^2$ of 17-AAG or an equivalent amount (on a molar basis) of a 17-AAG or 17-AG prodrug. In one embodiment, the dose is about 340 mg/m$^2$ of 17-AAG or an equivalent amount (on a molar basis) of a 17-AAG or 17-AG prodrug. In one embodiment, this dose is administered twice weekly for at least two weeks. In one embodiment, this dose is administered twice weekly for at least two weeks in a three week period, which rate of dosing per three week period is called a cycle, and multiple cycles of such treatment are administered to the subject.

In one embodiment, the therapeutically effective dose of 17-AAG or a prodrug of 17-AAG is a dose that results in an $AUC_{total}$ of 17-AAG per dose in the range of about 12,500 ng/mL*h to 25,000 ng/mL*h. In one embodiment, this dose is administered at a rate and frequency such that the $C_{max}$ of 17-AAG does not exceed 15,000 ng/mL. In one embodiment, this dose is administered at a rate and frequency such that the $C_{max}$ of 17-AAG is greater than 1,800 ng/mL. In one embodiment, this dose is administered at a rate and frequency such that the $C_{max}$ of 17-AAG is greater than 3,000 ng/mL. In one embodiment, this dose is administered at a rate and frequency such that the $C_{max}$ of 17-AAG is greater than 1,800 but does not exceed 15,000 ng/mL. In one embodiment, this dose is administered at a rate and frequency such that the $C_{max}$ of 17-AAG is greater than 3,000 but does not exceed 15,000 ng/mL.

In one embodiment, the therapeutically effective dose of 17-AG or a prodrug of 17-AG (which prodrug includes 17-AAG) is a dose that results in an $AUC_{total}$ of 17-AG per dose in the range of about 5,000 to 18,000 ng/mL*h. In one embodiment, this dose is administered at a rate and frequency such that the $C_{max}$ of 17-AG does not exceed 2,000 ng/mL. In one embodiment, this dose is administered at a rate and frequency such that the $C_{max}$ of 17-AG is greater than 500 ng/mL. In one embodiment, this dose is administered at a rate and frequency such that the $C_{max}$ of 17-AG is greater than 900 ng/mL. In one embodiment, this dose is administered at a rate and frequency such that the $C_{max}$ of 17-AG is greater than 500 but does not exceed 2,000 ng/mL. In one embodiment, this dose is administered at a rate and frequency such that the $C_{max}$ of 17-AG is greater than 900 but does not exceed 2,000 ng/mL.

In one embodiment, the therapeutically effective dose of 17-AAG, a prodrug of 17-AAG, 17-AG, or a prodrug of 17-AG is a dose that results in a combined $AUC_{total}$ of 17-AAG and 17-AG per dose in the range of about 17,500 to 43,000 ng/mL*h. In one embodiment, this dose is administered at rate and frequency such that the $C_{max}$ of 17-AAG does not exceed 15,000 ng/mL and/or the $C_{max}$ of 17-AG does not exceed 2,000 ng/mL. In one embodiment, this dose is administered at a rate and frequency such that the $C_{max}$ of 17-AAG is greater than 1,800 ng/mL and/or the $C_{max}$ of 17-AG is greater than 500 ng/mL. In one embodiment, this dose is administered at a rate and frequency such that the $C_{max}$ of 17-AAG is greater than 3,000 ng/mL and/or the $C_{max}$ of 17-AG is greater than 900 ng/mL. In one embodiment, this dose is administered at a rate and frequency such that the $C_{max}$ of 17-AAG is greater than 1,800 but does not exceed 15,000 ng/mL and/or the $C_{max}$ of 17-AG is greater than 500 but does not exceed 2,000 ng/mL. In one embodiment, this dose is administered at a rate and frequency such that the $C_{max}$ of 17-AAG is greater than 3,000 but does not exceed 15,000 ng/mL and/or the $C_{max}$ of 17-AG is greater than 900 but does not exceed 2,000 ng/mL.

In one embodiment, the therapeutically effective dose of 17-AAG or a prodrug of 17-AAG is a dose that results in a Terminal $t_{1/2}$ of 17-AAG in the range of 3 to 4.5 h. In one embodiment, the therapeutically effective dose of 17-AAG or a prodrug of 17-AAG is a dose that results in a Terminal $t_{1/2}$ of 17-AAG in the foregoing range and an $AUC_{total}$ of 17-AAG per dose in the range of about 12,500 to 25,000 ng/mL*h.

In one embodiment, the therapeutically effective dose of 17-AG or a prodrug of 17-AG is a dose that results in a Terminal $t_{1/2}$ of 17-AG in the range of 4 to 7 h. In one embodiment, the therapeutically effective dose of 17-AG or a prodrug of 17-AG is a dose that results in a Terminal $t_{1/2}$ of 17-AG in the foregoing range and an AUC$_{total}$ of 17-AG per dose in the range of about 5,000 to 18,000 ng/mL*H.

In one embodiment, the therapeutically effective dose of 17-AAG or a prodrug of 17-AAG is a dose that results in a Volume of distribution V$_z$ of 17-AAG in the range of 100 to 270 L. In one embodiment, the therapeutically effective dose of 17-AAG or a prodrug of 17-AAG is a dose that results in a Volume of distribution V$_z$ of 17-AAG in the foregoing range and an AUC$_{total}$ of 17-AAG per dose in the range of about 12,500 to 25,000 ng/mL*h.

In one embodiment, the therapeutically effective dose of 17-AAG or a prodrug of 17-AAG is a dose that results in a Clearance in the range of 30 to 50 L/h. In one embodiment, the therapeutically effective dose of 17-AAG or a prodrug of 17-AAG is a dose that results in a Clearance of 17-AAG in the foregoing range and an AUC$_{total}$ of 17-AAG per dose in the range of about 12,500 to 25,000 ng/mL*h.

In one embodiment, the therapeutically effective dose of 17-AAG or a prodrug of 17-AAG is a dose that results in a V$_{ss}$ in the range of 100 to 150 L. In one embodiment, the therapeutically effective dose of 17-AAG or a prodrug of 17-AAG is a dose that results in a V$_{ss}$ of 17-AAG in the foregoing range and an AUC$_{total}$ of 17-AAG per dose in the range of about 12,500 to 25,000 ng/mL*h.

BRIEF DESCRIPTION OF THE DRAWING(S)

Figure 7:
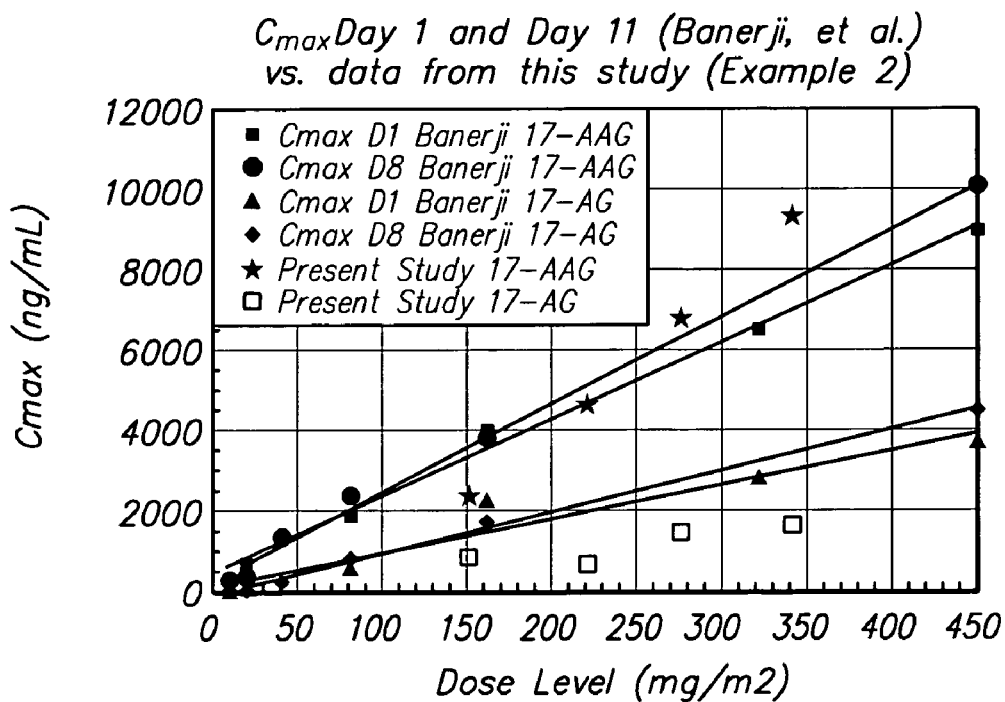

FIG. 7 shows the mean C$_{max}$ observed in the present study for 17-AAG and 17-AG compared to the mean C$_{max}$ reported Banerji et al. (2002) for 17-AAG on Day 1, 17-AAG on Day 8, 17-AG on Day 1, and 17-AG on Day 8.

Figure 8:
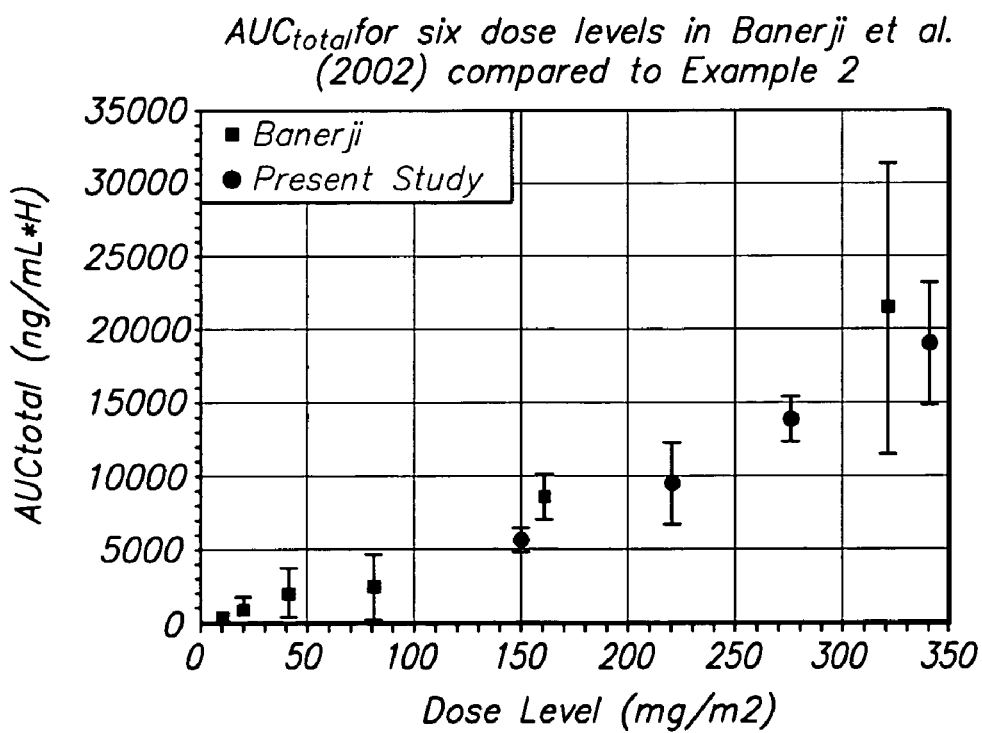

FIG. 8 shows the mean AUC$_{total}$ of 17-AAG observed in the present study in compared to the mean AUC$_{total}$ of 17-AAG reported in Banerji et al. (2002).

Figure 9:
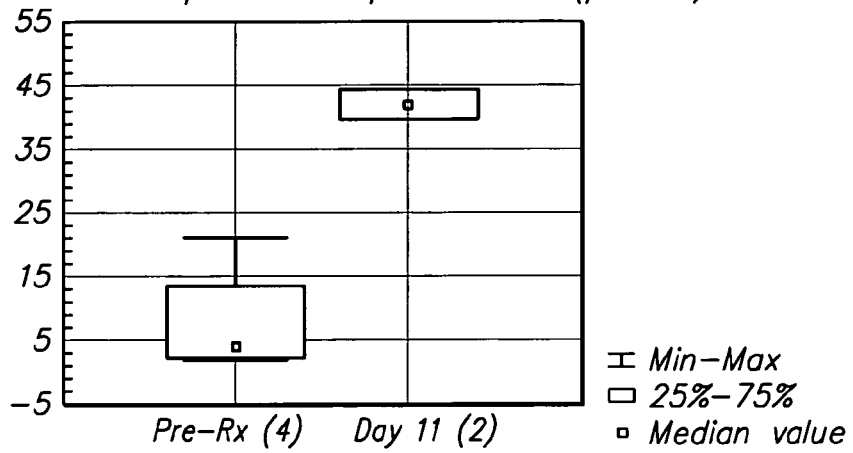

FIG. 9 shows the percent of CD138$^+$ cells with abnormal mitochondrial potential in BM for patients during pre-treatment and on Day 11 of treatment (after four infusions of 17-AAG).

Figure 10:
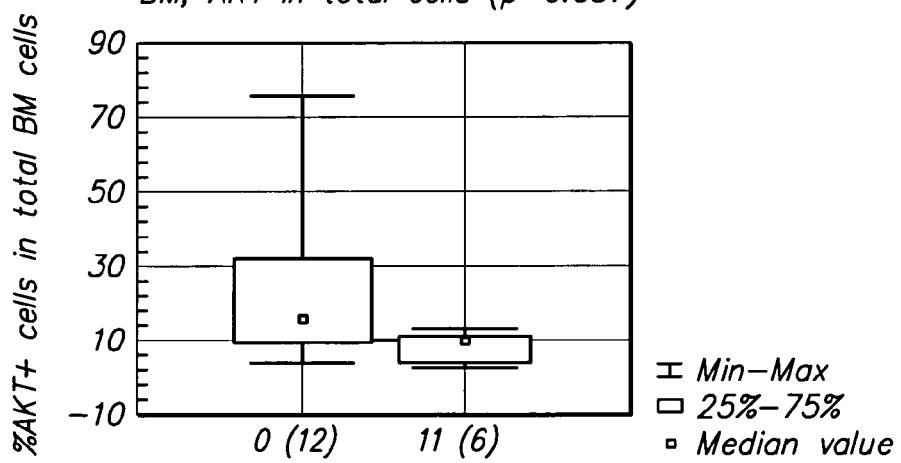

FIG. 10 shows the percent AKT$^+$ cells in total BM cells for patients during pre-treatment and on Day 11 of treatment (after four infusions of 17-AAG).

Figure 11A:
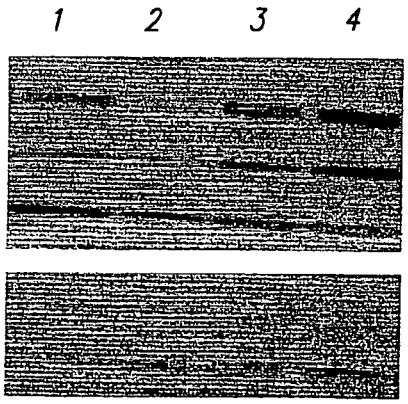

FIGS. 11A (275 mg/m$^2$ doses) and 11B (340 mg/m$^2$ doses) show immunoblots of Hsp70, total AKT, ILK, raf-1, and LCK from samples taken at 0 hours and 4 hours after administration on Day 1 and Day 4 (all data from Cycle 1 of treatment; 1: Day 1, 0 hour; 2: Day 1, 4 hours; 3: Day 11, 0 hour; 4; Day 11, 4 hours).

Figure 12:
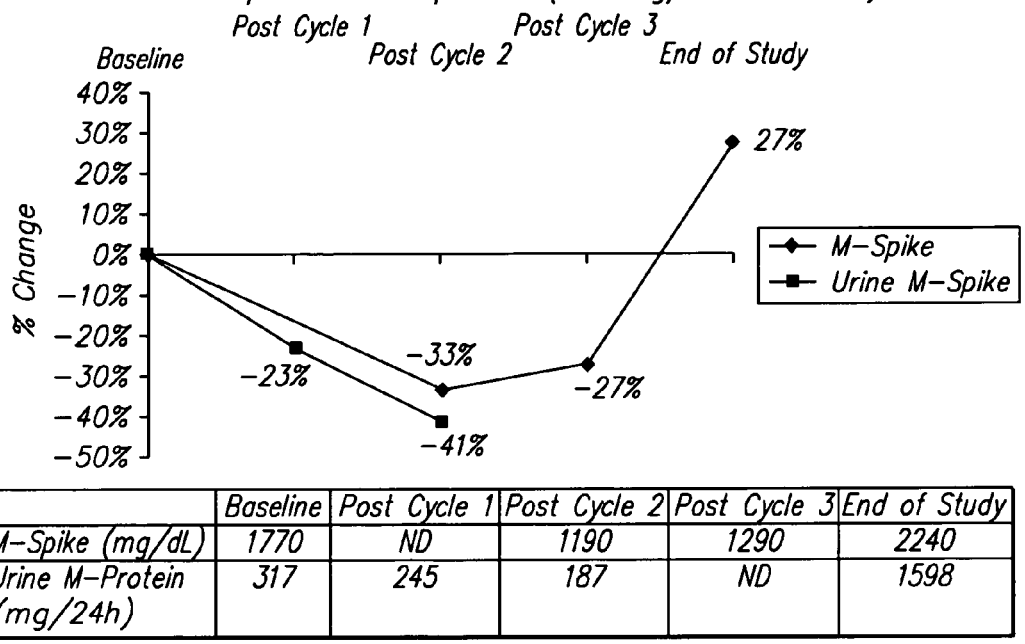

FIG. 12 shows the percent change of serum M-spike and urine M-protein of a patient treated at the 150 mg/m$^2$ of 17-AAG dose level.

Figure 13:
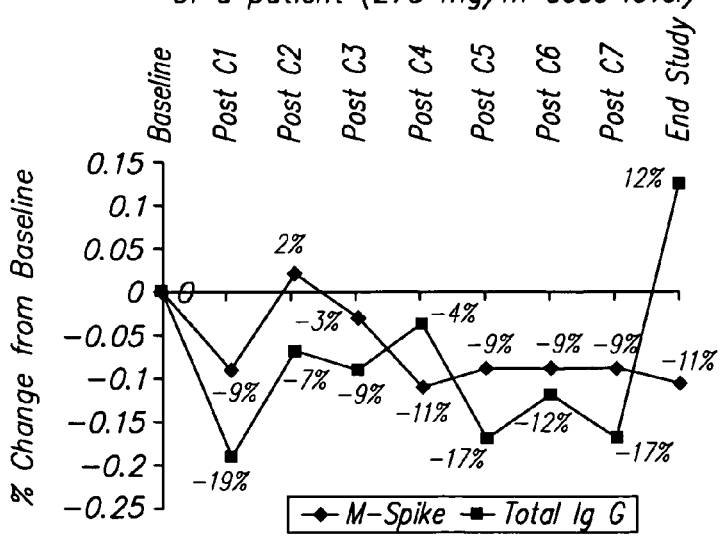

FIG. 13 shows the percent change of serum M-spike and total IgG of a patient treated at the 275 mg/m$^2$ of 17-AAG dose level.

DETAILED DESCRIPTION OF THE INVENTION

Definitions

To aid in understanding and practice of the present invention, definitions for certain terms used herein are provided below.

"Adverse effects" are as defined in National Cancer Institute (2003).

A "dose limiting toxicity" (DLT) is defined as any of the following clinical toxicities, referencing National Cancer Institute (2003). Hematologic toxicities comprise: (1) Grade 4 neutropenia (absolute neutrophil count (ANC)<0.5×10$^9$/L) for more than 5 consecutive days, or febrile neutropenia (ANC<1.0×10$^9$/L, fever≧38.5° C.), (2) Grade 4 thrombocytopenia (platelets<25.0×10$^9$/L or bleeding episode requiring platelets transfusion), and/or Grade 4 anemia (Hemoglobin<6.5 g/dl). Non-Hematologic toxicities comprise: (1) any≧Grade 3 non-hematologic toxicity (except Grade 3 injection site reaction, alopecia, anorexia, fatigue), (2) nausea, diarrhea and/or vomiting of Grade≧3 despite the use of maximal medical intervention and/or prophylaxis, and/or (3) treatment delay of more than 4 weeks due to prolonged recovery from a drug-related toxicity.

"Complete response (CR)" is defined on the basis of negative immunofixation ("IF") on both serum and urine, maintained for at least 6 weeks. A bone marrow aspirate ("BMA") containing <5% plasma cells can be used to confirm a CR. A trephine biopsy is performed, and the results indicate <5% plasma cells. In non-secretory myeloma, the marrow biopsy is repeated after a 6-week interval to confirm a CR. No increase in the size or number of lytic lesions should occur (development of a compression fracture does not exclude response), with disappearance of soft tissue plasmacytomas. (Bladé et al., 1998).

"KPS performance status" is as defined in Table 1, which also provides a comparison against the ECOG scale.

TABLE 1

| KPS Performance Status | | | |
|---|---|---|---|
| Karnofsky Scale | | ECOG Scale | |
| Normal, no complaints | 100 | Fully active, able to carry on all pre-disease performance without restriction | 0 |
| Able to carry on normal activity, minor signs or symptons of disease | 90 | | |

TABLE 1-continued

KPS Performance Status

| Karnofsky Scale | | ECOG Scale | |
|---|---|---|---|
| Normal activity with effort | 80 | Restricted in physically strenuous activity but ambulatory and able to carry out work of a light or sedentary nature (e.g., office work or light house work) | 1 |
| Unable to carry on normal activity or perform active work; cares for self | 70 | | |
| Requires occasional assistance but is able to care for most own needs | 60 | Ambulatory and capable of all self-care but unable to carry out any work activities; up and about more than 50% of waking hours | 2 |
| Requires considerable assistance and frequent medical care | 50 | | |
| Disabled; requires special medical care and assistance | 40 | Capable of only limited self-care, confined to bed or chair more than 50% of waking hours | 3 |
| Severely disabled; hospitalization indicated although death not imminent | 30 | | |
| Very sick; hospitalized and active | 20 | Completely disabled; cannot perform any self-care; totally confined to bed or chair | 4 |
| Moribund; fatal processes progressing rapidly | 10 | | |
| Dead | 0 | | |

"Minimal response" is defined as one or more of the following: between 25-49% reduction in serum M-protein, maintained for at least six weeks; between 50-89% reduction in urinary light chain excretion which still exceeds 200 mg/24 hours, maintained for at least 6 weeks; for patients with non-secretory myeloma only, between 25-49% reduction in plasma cells in a BMA or a bone trephine biopsy, if biopsy is performed, maintained for at least 6 weeks; between 25-49% reduction in the size of soft tissue plasmacytomas (by radiography or clinical examination); and no increase in the size or number of lytic lesions (development of a compression fracture does not exclude response). (Bladé et al., 1998).

"No Change" is defined as not meeting the criteria of either minimal response or progressive disease. (Bladé et al., 1998.)

"Partial response (PR)" is defined as occurring in patients in whom some, but not all, of the criteria for CR have been met, including those in whom routine electrophoresis is negative but on whom IF has not been performed. See Bladé et al. (1998), which provides examples.

"Plateau phase" is defined on the basis of stable paraprotein levels for a minimum of 3 months. Plateau will require observations to be within 25% of the value when response is assessed, a rise above 25% being one of the criteria for disease progression. (Bladé et al., 1998.)

"Progression of disease," for patients not in CR, is defined as a definite increase in disease activity in patients in partial remission or plateau phase, whereas the term relapse applies to a recurrence of evident disease in patients previously in CR. See Bladé et al. (1998), which provides examples.

"Refractory cancer" means a cancer that has not responded to one or more previous treatments.

"Relapse" means the return of signs and symptoms of cancer after a period of improvement from one or more previous treatment. "Relapse from CR" is defined as one or more of the following: a reappearance of serum or urinary paraprotein on IF or routine electrophoresis, confirmed by at least one further investigation and excluding oligoclonal reconstitution; a greater than 5% plasma cells in a BMA or on trephine bone biopsy; development of new lytic bone lesions or soft tissue plasmacytomas or definite increase in the size of residual bone lesions (development of a compression fracture does not exclude continued response and may not indicate progression); and development of hypercalcemia (corrected serum calcium greater than 11.5 mg/dL) not attributable to any other cause.

"Therapeutically effective dose" means, unless otherwise indicated, the amount of drug that is required to be administered to achieve the desired therapeutic result.

Embodiments

The present invention provides important new methods for using 17-AAG or 17-AG and their prodrugs that exert their anti-cancer effect through the in vivo formation of 17-AAG or 17-AG to treat MM. In one embodiment of the methods of the present invention, 17-AAG, or a prodrug of 17-AAG, is the only therapeutic agent in the pharmaceutical formulation administered to the patient to treat MM. The present invention arose in part from the discovery of new methods for dosing and administering 17-AAG to achieve and maintain therapeutically effective blood levels of 17-AAG or 17-AG (or blood levels of 17-AAG added together with 17-AG, as these moieties are equipotent in cellular assays), expressed as $AUC_{total}$, $C_{max}$, Terminal $t_{1/2}$, Clearance, and/or Volume of distribution, expressed as either $V_z$ or $V_{ss}$, without reaching blood levels likely to cause unmanageable toxicity.

In one embodiment, the present invention comprises administering multiple doses of 17-AAG, or a prodrug of 17-AAG, over a period of three weeks. Collectively, these doses over the three week period are called a cycle. A patient may be treated with multiple cycles of therapy. Different cycles, including cycles of longer or shorter duration or involving greater or fewer doses than described specifically herein, can be used to practice the present invention, so long as the therapeutically effective doses described herein are achieved.

In one embodiment, the therapeutically effective dose is achieved by the administration of multiple doses of 17-AAG, or a prodrug of 17-AAG, to a patient with MM over a time period of at least 3 weeks, wherein such multiple doses result in an $AUC_{total}$ for 17-AAG per dose of at least 12,500 ng/ml*h but does not exceed 25,000 ng/ml*h. In one embodiment, four doses are administered per cycle, with each dose being at least 150 mg/m$^2$, and a period of 3 to 4 days between each dose. In another embodiment, four doses are administered per cycle, with two doses per week administered for the first two weeks of the three week cycle.

Compounds other than 17-AAG or 17-AG can be administered that are converted in vivo to 17-AAG or 17-AG (prodrugs). One type of prodrug is that in which the benzoquinone ring is reduced to a hydroquinone ring, but is metabolized back to a benzoquinone ring in the subject. A specific example of a 17-AAG prodrug is 17-allylamino-18,21-dihydro-17-demethoxygeldanamycin. (Adams et al., 2005). The methods of the present invention therefore include, in one embodiment, a method for treating MM in a patient in need of said treatment, wherein the method comprises the administration of multiple doses of 17-AAG or 17-AG, or a prodrug of 17-AAG or 17-AG, to a subject with MM, over a time period of at least 3 weeks, wherein such multiple doses result in an $AUC_{total}$ for 17-AG per dose of at least 5,000 but does not exceed 18,000 ng/mL*h. In one embodiment, four doses are administered per cycle, with each dose being at least 150 mg/m$^2$, and a period of 3 to 4 days between each dose. In another embodiment, four doses are administered per cycle, with two doses per week administered for the first two weeks of the three week cycle.

Thus, the present invention includes within its scope the use of prodrugs of 17-AAG and the term "administering" encompasses the treatment of MM with a pharmaceutically equivalent amount of a compound that converts to 17-AAG or 17-AG in vivo after administration to the subject in need thereof. Conventional procedures for the selection and preparation of suitable prodrug derivatives are described in Wermuth, 2003.

The subject in need of treatment, for purposes of the present invention, is typically a human patient suffering from MM, although the methods of the invention can be practiced for veterinary purposes, with suitable adjustment of the unit dose to achieve the equivalent $AUC_{total}$ or other PK and PD parameters described herein for the particular mammal of interest (including cats, cattle, dogs, horses, and the like). Those of skill in the art of pharmaceutical science know or can readily determine the applicable conversion factors for the species of interest. Typically, however, the methods will be practiced to benefit human subjects, and those subjects will typically have exhibited some histological evidence of MM, including one or more of the following: M-spike in serum or urine, BM plasmacytosis of >30%, anemia, renal failure, hypercalcemia, and/or lytic bone lesions.

In one embodiment, the subject has been diagnosed with Stage III MM under the Durie-Salmon system and exhibits one or more of these symptoms: hemoglobin value <8.5 g/dL, serum calcium value >12 mg/dL, advanced lytic bone lesions (scale 3), high M-component production rate (IgG value >7 g/dL; IgA value >5 g/dl; Bence Jones protein >12 g/24 hour). Alternatively, the subject has been diagnosed with Stage III MM based on the International Staging System (ISS) system, with serum levels of β-2 microglobulin >5.5 g/dL.

In another embodiment, the patient will have been diagnosed with Stage II MM based on the Durie-Salmon system, wherein the subject does not have Stage III MM (based on the Durie-Salmon system) and has one or more but does not have all of the following symptoms: hemoglobin value >10 g/dL, serum calcium value ≦12 mg/dL, bone x-ray, normal bone structure (scale 0) or solitary bone plasmacytoma only, low M-component production rate (IgG value <5 g/dL; IgA value <5 g/dL). In another embodiment, the patient will have been diagnosed with Stage II MM based on the ISS system, wherein the subject does not have Stage III MM (based on the ISS system) and does not have serum levels of β-2 microglobulin <3.5 g/dL and albumin ≧3.5 g/dL.

In another embodiment, the patient will have one or more of the following signs or symptoms of MM: an elevated level of serum M protein (such as >3 g/dL), and/or more than 10% of the cells in a BM sample from the subject are plasma cells. In another embodiment, prior to treatment the Karnofsky performance status (KPS) of the patient is at least 70%. In another aspect, the KPS of the patient is at least 60%, 50%, 40%, 30%, 20%, or 10%. In one aspect, the ECOG of the patient is at least 0, 1, 2, or 3.

A therapeutically effective dose of 17-AAG, 17-AG, or a prodrug or either 17-AAG or 17-AG is the amount of 17-AAG that is administered at each administration over one treatment cycle to the subject that brings about a therapeutic result. The therapeutic result can be that the rate of the progression or spread of the cancer is slowed or stopped for some period of time. In some patients, the therapeutic result can be complete elimination of MM. In some patients, a therapeutic result will be achieved with one treatment cycle. In other patients, a therapeutic result will be achieved only after multiple cycles of treatments. As those of skill in the art will appreciate, however, there can be no assurance that every MM patient will achieve a therapeutic result.

As noted above, in one embodiment, each treatment cycle is three weeks. In other embodiments, other treatment cycle times can be employed, such as two or four weeks (or one month), so long as the equivalent $AUC_{total}$ or other PK and PD parameters described herein are achieved. The unit dose employed in each cycle is administered at least once and up to eight times per treatment cycle. Typically, the dose is administered two to four times per treatment cycle. In one embodiment, the dose is administered twice weekly for 2 weeks out of each treatment cycle of three weeks. For example, if one starts a cycle at the administration of the first dose, then in one embodiment, the unit dose is administered once or twice in the first two weeks of the treatment cycle and not during the third week. In one embodiment, the dose is administered on days 1, 4, 8, and 11 of each treatment cycle, with day 1 being the day the first dose is administered.

Each dose of 17-AAG is a dose of not more than the maximally tolerable dose ("MTD"), which can be defined as the maximum dose at which less than two or fewer of six subjects undergoing the method of treatment experience hematologic or non-hematologic toxicity that is not amenable to supportive care. Preferably, the amount of 17-AAG administered is equal to or less than the MTD. Preferably, the amount of 17-AAG administered is one that does not result in unacceptable and/or unmanageable hematologic or non-hematologic toxicity. Preferably, the MTD is about 340 mg/m$^2$ per dose.

The therapeutically effective amount of a unit dose 17-AAG or 17-AG or a prodrug of either is the amount that, after one or more cycles of administration in accordance with this invention, results in a complete response (CR), a partial response (PR), a minimal response (MR), a stable disease (StD) condition, a reduction of serum monoclonal protein (serum M protein), or a reduction of plasma cells in the BM of the subject (Bladé et al., 1998), for at least a period of time, such as 3 weeks, 6 weeks, 6 months, one year, or several years. In one embodiment, the administration of 17-AAG results in a decrease in serum and/or urine M protein, BM plasmocytosis, alleviation of anemia, alleviation of renal failure, alleviation of hypercalcemia, and/or reduction/alleviation of lytic bone lesions in the MM patient. In one embodiment, some patients will not relapse from a CR or will experience a significant delay in the progression of the disease.

The amount of 17-AAG administered in a single unit dose can range from 275 to 340 mg/m$^2$ per dose. Where the 17-AAG is administered twice weekly for two out of every three weeks, the amount of 17-AAG administered ranges from 275 to 340 mg/m$^2$ per dose. Those of skill in the art will recognize that the unit dose amounts of 17-AAG or 17-AG prodrugs or 17-AG itself can be calculated from the doses provided herein for 17-AAG and the molecular weight and relative bioavailability of the prodrug or 17-AG.

The method of the invention can also be described in terms of the amount of 17-AAG administered per treatment cycle. The per cycle amount will typically be at least 1,100 mg/m$^2$. Typically the per cycle amount will be at least 1,360 mg/m$^2$. In various embodiments, the amount of 17-AAG administered is at least 1,100 to 1,360 mg/m$^2$/treatment cycle.

As noted above, the frequency of the administration of the unit dose is once weekly or twice weekly. In one embodiment of the method of the invention, the pharmaceutical formulation is administered intravenously twice weekly for 2 weeks every 3 or 4 weeks. In one embodiment, the patient is administered a pre-treatment medication to prevent or ameliorate treatment related toxicities. Such pre-treatment medications are described in the examples below. In one embodiment of the method of the invention, the administration of 17-AAG or 17-AG or a prodrug of either is performed on day 1, 4, 8 and 11 of each cycle, and the cycle time is 3 weeks. 17-AAG will typically be administered by intravenous infusion, infused in a period of at least 30, 60, 90, or 120 minutes. For patients with a body surface area ("BSA") greater than 2.4 m$^2$, dosing can be calculated in accordance with the methods herein using a maximum BSA of 2.4 m$^2$.

In human clinical trials of the method of the invention, the following administration regimens have been employed without reaching dose limiting toxicity ("DLT") in any treated patient: 275 mg/m$^2$ per single administration of 17-AAG twice weekly for two out of three weeks (Days 1, 4, 8, and 11, with a cycle time of 21 days).

As noted above, after 17-AAG is administered, the major metabolite 17-AG, having anti-cancer activity in its own right, appears in the subject. 17-AAG and 17-AG are thus each, and together, responsible for the therapeutic benefit of the method of the invention. The therapeutically effective dose and dosing regimen of 17-AAG is one that achieves an Area Under Curve (AUC$_{total}$) of 17-AAG and/or 17-AG in the subject as described herein. Various therapeutically effective doses and dose regimen are illustrated in the examples below. Therapeutically effective doses and dosing regimen of 17-AAG and/or 17-AG provided by the present invention can also be described in terms of Terminal Half Life (t$_{1/2}$); Clearance (CL); and/or Volume of Distribution in the elimination phase or steady state (V$_z$ and/or V$_{ss}$).

The therapeutic benefit from the treatment method of the present invention can be observed in responding subjects as soon as 3, 6, 12, 18 or 24 weeks from the start of treatment. In one embodiment, a therapeutic benefit from the treatment is a reduction in a serum protein, and/or BUN or serum calcium, of the patient. In various embodiments, the reduction is at least 25%; at least 50% to 80%; at least 90%; and 100%. The reduction in serum M protein can be determined, for example, by serum protein electrophoresis or immuno-fixation techniques. The percent reduction is the level of the serum protein, BUN, or calcium in the patient, measured after a period of treatment and then compared to the level of the serum M protein, BUN, or calcium in the patient measured just prior to treatment. Serum proteins are proteins that, when present in elevated levels in the serum, indicate the subject suffers from MM. Such serum proteins include, but are not limited to, serum M protein (also known as serum M paraprotein), β2-microglobulin, light chain, and total protein.

Other therapeutic benefits that can be achieved via the present invention include one or more of the following: decrease in BM plasmaocytosis, alleviation of anemia, alleviation of renal failure, alleviation of hypercalcemia, and/or reduction/alleviation of lytic bone lesions. Another therapeutic benefit is an improvement of the KPS of the patient by 10% or more, 20% or more, 30% or more, 40% or more, or 50% or more. Another therapeutic benefit is an improvement of the ECOG of the patient by 1 or more, 2 or more, or 3 or more.

Ideally, practice of the present invention does not result in unmanageable hematologic or non-hematologic toxicity. Hematologic toxicities to be avoided include: Grade 4 neutropenia, Grade 4 thrombocytopenia, and/or Grade 4 anemia. Non-hematologic toxicities include: any ≧Grade 3 non-hematologic toxicity (except Grade injection site reaction, alopecia, anorexia, and/or fatigue), nausea, diarrhea and/or vomiting ≧Grade 3 (despite use of maximal medical intervention and/or prophylaxis), and/or treatment delay of more than 4 weeks due to prolonged recovery from a drug related toxicity. Those of skill in the art will recognize that various toxicities may occur in a cancer patient; the method of the present invention provides the benefit of reduced or elimination of the occurrence of such toxicities.

Where the pharmaceutical formulation comprises an additional compound that might cause an anaphylactic reaction (like Cremophor®), additional medications can be administered to prevent or reduce the anaphylactic reaction, such as (a) loratidine or diphenhydramine, (b) famotidine, and (c) methylprednisone or dexamethasone.

The present invention also provides, in various embodiments, methods for treating MM by administering 17-AAG or 17-AG or a prodrug of either in combination with another anti-cancer compound, which can be, for example, Thalomid®, Aredia®, and Zometa® or Revlimid® (lenalidomide). The other anti-cancer drug or agent can be administered in unit doses and dosing regimen currently employed in the art.

Importantly, the present invention can be used to treat patients with MM who have failed at least one prior anti-cancer therapy regimen, that is, have refractory or relapsed refractory MM. These prior anti-cancer therapies include, but are not limited to, monotherapy (single agent therapy) or combination therapies of the following treatments and anti-cancer agents: chemotherapy, stem cell transplantation, Thalomid®, Velcade®, and Revlimid®. Chemotherapy includes treatment with a combination melphalan and prednisone (MP), VAD, or an alkylating agent alone or in combination with other agent(s), such as cyclophosphamide plus etoposide or combinations of etoposide, dexamethasone, doxorubicin.

Diagnostic and laboratory methods and tests that may be of benefit in practice of the present invention are well known to one of ordinary skill in the art. See, for example, Pagana and Pagana, Mosby's Manual of Diagnostic and Laboratory Tests, 2d Ed., Mosby-Year Book, 2002 and Jacobs & DeMott Laboratory Test Handbook, 5th Ed., Jacobs et al. (eds), Lexi-Comp, Inc., 2001 (each incorporated herein by reference). Free kappa and free lambda light chain concentrations in serum can be measured using Freelite™ (The Binding Site Inc., Birmingham, United Kingdom).

An active pharmaceutical ingredient ("API," 17-AAG, 17-AG, prodrug, other anti-cancer compound, etc.) useful in the method of the present invention can be formulated for administration orally or intravenously, in a suitable solid or liquid form. See Gennaro, ed., Remington: *The Science and Practice of Pharmacy*, 20th Ed. (Lippincott Williams & Wilkins 2003), incorporated herein by reference. The API can be compounded, for example, with a non-toxic, pharmaceutically acceptable carrier or excipient for solutions, emulsions, suspensions, or any other form suitable for enteral or parenteral administration. Pharmaceutically acceptable carriers include water and other carriers suitable for use in manufacturing preparations in liquefied form. In addition, auxiliary stabilizing, thickening, and coloring agents may be used.

An API useful in the method of the invention may be formulated as micro-capsules, nanoparticles, or nanosuspensions. General protocols for such formulations are described, for example, in Microcapsules and Nanoparticles in Medicine and Pharmacy by Max Donbrow, ed., CRC Press (1992) and in Bosch et al. (1996), De Castro (1996), and Bagchi et al. (1997). By increasing the ratio of surface area to volume, these formulations are especially suitable for the delivery of 17-AAG or another relatively insoluble API.

17-AAG can be formulated in an emulsion with vitamin E or a PEGylated derivative thereof. Generic approaches to formulations with such excipients are described in Quay et al. (1998) and Lambert et al. (2000). The 17-AAG can be dissolved in an aqueous solution containing ethanol (preferably less than 1% w/v). Vitamin E or a PEGylated-vitamin E is added. The ethanol is then removed to form a pre-emulsion that can be formulated for intravenous or oral routes of administration.

Another method for preparing a pharmaceutical formulation useful in the present method involves encapsulating 17-AAG in liposomes. Methods for forming liposomes as drug delivery vehicles are well known in the art. Suitable protocols adaptable for the present invention include those described by Boni et al. (1997), Straubinder et al. (1995), and Rahman et al. (1995) for paclitaxel and by Sonntag et al. (2001) for epothilone, mutatis mutandis. Of the various lipids that may be used in such formulations, phosphatidylcholine and polyethyleneglycol-derivatized distearyl phosphatidylethanoloamine are noteworthy.

The amount of 17-AAG or other API that may be combined with the carrier materials to produce a single or unit dosage form will vary depending upon the subject treated and the particular mode of administration. For example, a formulation for intravenous use comprises an amount of 17-AAG ranging from about 1 mg/mL to about 25 mg/mL, preferably from about 5 mg/mL, and more preferably about 10 mg/mL. Intravenous formulations are typically diluted between about 2 fold and about 30 fold with water for injection (WFI), normal saline, or 5% dextrose solution prior to use. In many instances, the dilution is between about 5 and about 10 fold.

In one embodiment of the method of the invention, 17-AAG is formulated as a pharmaceutical solution formulation comprising 17-AAG dissolved in a vehicle comprising (i) a first component that is ethanol; (ii) a second component that is a polyethoxylated castor oil; and (iii) a third component selected propylene glycol, PEG 300, PEG 400, glycerol, and combinations thereof, as disclosed in Zhong et al. (2005).

Another formulation of 17-AAG that may be used is one based on dimethylsulfoxide ("DMSO") and egg lecithin (egg phospholipids), as taught in Tabibi et al. (2004). However, because of certain characteristics of DMSO (odor, patient adverse reactions), such formulations are less preferred than the DMSO-free ones taught herein.

Other formulations for 17-AAG that may be employed in the method of the invention are described in Ulm et al. (2003), Ulm et al. (2004), Mansfield et al. (2006), Desai et al. (2006), and Isaacs et al. (2006).

In another embodiment, the pharmaceutical formulation can be diluted 1:7 prior to administration with sterile WFI, USP (one part undiluted drug product to 6 parts sterile WFI). Dilution is performed under controlled, aseptic conditions. The final diluted drug product concentration is, using 17-AAG as an example, at least 1.00 mg/mL, such as approximately 1.43, approximately 2.00 or approximately 10.00 mg/mL.

Depending on the BSA and the assigned dose for the subject, the dose of 17-AAG or other API will require different volumes of drug product to be added to the admixture bag. An overfill can be calculated and employed to account for loss in the administration set. Preferably, the pharmaceutical formulation, with the diluted drug product, is pH neutral, and the solution is hypertonic at approximately 600 mOsm. The pharmaceutical formulation can be stored at −20° C., with protection from light. Drug product is allowed to come to room temperature prior to admixture and then is mixed is by gentle inversion. After dilution, the drug product should stable for up to about 10 hours at room temperature (at a dilution of 1:7).

The present invention, having been described in summary fashion and in detail above is illustrated in the following Examples.

Example 1

Pharmacokinetics of 17-AAG in the Cremophor®-based Formulation in Dogs

Prior clinical reports of 17-AAG in cancer involved trials in which the 17-AAG was administered in a formulation comprised of DMSO with egg phospholipids (Tabibi et al 2004 and 2005). To compare the PK of this formulation of 17-AAG with the Cremophor®-based formulation to be used in the clinical trial reported in Example 2, each formulation of 17-AAG was administered at two doses (1 and 2 mg/kg; 20 and 40 mg/m²) to beagle dogs. Six dogs received the 1 mg/kg dose, and 5 dogs received the 2 mg/kg dose, in a crossover design, so that each dog received both formulations. The results, summarized in the table below, show that the Cremophor®-based formulation is comparable to the DMSO/egg phospholipid formulation. Mean AUC is within 20%; $C_{max}$, $T_{max}$, and elimination half-life values were also similar for the two formulations.

TABLE 2

Pharmacokinetic Parameters (Mean ± SD)

| Formulation | Dose level (mg/kg) | N | $C_{max}$ (ng/mL) | $T_{max}$ (hrs) | $AUC_{0-\infty}$ (ng-h/mL) | $t_{1/2}$ (hrs) |
|---|---|---|---|---|---|---|
| DMSO/egg lecithin | 1 | 6 | 278 ± 27 | 1.00 | 392 ± 20 | 2.0 |
| Cremophor® based | 1 | 6 | 322 ± 37 | 1.00 | 459 ± 59 | 1.9 |

TABLE 2-continued

Pharmacokinetic Parameters (Mean ± SD)

| Formulation | Dose level (mg/kg) | N | $C_{max}$ (ng/mL) | $T_{max}$ (hrs) | $AUC_{0-\infty}$ (ng-h/mL) | $t_{1/2}$ (hrs) |
|---|---|---|---|---|---|---|
| DMSO/egg lecithin | 2 | 5 | 643 ± 126 | 0.958 | 853 ± 181 | 2.1 |
| Cremophor ® based | 2 | 5 | 788 ± 143 | 0.900 | 1,057 ± 155 | 2.2 |

Example 2

Treatment of Patients with Multiple Myeloma with 17-AAG

The method of the invention was tested in an open-label, dose escalating clinical trial. The trial was designed to establish the MTD of 17-AAG administered by IV infusion over 60 minutes, on Days 1, 4, 8, and 11 of a dosing cycle lasting 3 weeks. The trial was designed with a dose-escalating component in which the dose of 17-AAG was escalated from 150 mg/m² to the MTD.

Disease response evaluations were performed following every two cycles of treatment (approximately every 6 weeks). The determination of anti-tumor efficacy in stable or responding patients was based on objective tumor assessments made according to a standardized myeloma response assessment system.

All baseline imaging-based tumor assessments were were performed within 28 days prior to the start of treatment and were reevaluated every 6 weeks (approximately every two cycles) thereafter. All patients with responding tumors (CR or PR) were examined to confirm the response 6 weeks after the first documentation of response. Response criteria used were according to Bladé et al. (1998).

Pharmacokinetic (PK) and pharmacodynamic (PD) sampling was obtained during the first treatment cycle only. In the event of drug-related serious adverse events (SAEs) and/or Grade 4 toxicities, additional PK samples were collected.

MM patients enrolled in this study were those who had failed at least two prior anti-cancer therapy regimens. The enrollment criteria were: (1) patients were at least 18 years old; (2) had a KPS performance status of ≧70%; (3) had histologic evidence of MM but did not necessarily have measurable disease, although disease had to have been assessed within 28 days prior to treatment initiation; (4) were, with respect to all adverse events of any prior chemotherapy, surgery, or radiotherapy, resolved to NCI CTCAE (v. 3.0) Grade ≦2; and (5) had the following laboratory results within 10 days of 17-AAG administration: hemoglobin ≧8 g/dL, absolute neutrophils count ≧1.5×10⁹/L, platelet count ≧75×10⁹/L, serum bilirubin ≦2×upper limit of normal (ULN), AST ≦2.5 ULN, and serum creatinine ≦2×ULN.

Patients were graded according to the KPS Performance Status scale and criteria as described in Table 1. Patients were excluded from the study if they had a condition such as pre-existing neuropathy, pregnancy, breast-feeding, recent chemotherapy, and so forth. To be eligible for enrollment, patients also had to meet certain hematologic conditions.

17-AAG is highly protein bound in plasma (approximately 95% in in vitro assays using human blood); however, the plasma protein to which the drug binds and the affinity of binding are not known. Patients who are receiving agents that are known to be highly protein bound were subjected to close clinical monitoring while enrolled in the trial. In vitro studies implicate the involvement of cytochrome P450 enzymes in the metabolism of 17-AAG. No formal drug-drug interaction studies have been performed with 17-AAG and drugs that are substrates, inhibitors, or inducers of cytochrome P450-3A4. While there is no contraindication to the concomitant use of any medication with 17-AAG, 17-AAG was used with caution in combination with drugs that are also highly protein bound (e.g. warfarin) and drugs that are a substrate, inhibitor, or inducer of cytochrome P450-3A4. Hormonal contraceptives were not used in women of childbearing potential enrolled in the trial. No other investigational agents were permitted during the entire duration of the study.

PK assessments included the following tests: Blood samples for determination of plasma concentrations of the parent compound and its primary metabolite were collected following the first and fourth 17-AAG administration only (Day 1 and 11). The total number of PK samples collected was approximately 110 mL of whole blood (7-8 tablespoons). If a patient experienced a potentially drug-related SAE, additional PK samples were collected. Blood was drawn from the contralateral arm to the infusion site using an indwelling catheter to avoid multiple needle sticks. For the 17-AAG samples, 5 mL of blood was drawn into a vacuum tube containing heparin as anti-coagulant. The blood tube was inverted several times, and the tube placed in wet ice immediately pending separation of the plasma. If a catheter was used for blood collection, the fluid in the catheter was completely withdrawn prior to each sample collection and discarded. Plasma samples were kept on wet ice during collection and centrifugation. Plasma samples were split into two cryovials prior to freezing at −70° C. Plasma concentrations of 17-AAG and its primary metabolite(s) were measured by a validated liquid chromatography-mass spectrometry method. (Egorin et al, 1998).

PD assessment included the following tests: The occurrence of specific toxicities (e.g., severity, duration and reversibility) was compared to PK parameters (e.g., clearance, exposure, elimination half-life, maximal plasma concentration, and time above a target plasma concentration). These toxicities included hepatotoxicity and gastrointestinal toxicities. The laboratory correlates included a) surface expression of insulin-like growth factor receptor-1 (IGF-1R) and b), total expression of Akt, Hsp90 and Hsp70. MM cells were purified from BMAs performed at baseline, within 24 hours of the first dose of 17-AAG, and after the end of treatment. MM cells were purified from the BMA based upon CD 138 expression using magnetic bead technology and confirmed by flow cytometric analysis to be >95% CD138+MM cells. Flow cytometric analysis was used to assess IGF-1R surface expression using fluorescein isothyocynate (FITC)-conjugated anti-human IGF-1R monoclonal antibody (Mitsiades et al., 2002). Immunoblotting analyses were used to evaluate the total levels of Akt, Hsp90 and Hsp70. BM aspirations are routinely performed to assess clinical status in MM. These correlative studies allowed a) assessment of the degree to which 17-AAG inhibited Hsp90 function in tumor cells from MM patients treated on protocol; and b) correlation of clinical responses to 17-AAG with the degree of modulation of the biomarkers. In addition, gene expression profiling (Davies et al., 2003) was used to identify other potential bio-markers for drug sensitivity versus resistance, which can be validated in future clinical trials. Finally, peripheral blood mononuclear cells were isolated on two occasions (the first and last infusion in Cycle 1, on Days 1 and 11) prior to and 4 hours following the infusion. Cells were examined for change in client protein expression by Western Blot. Client proteins of interest include Hsp70, RAF1, LCK and CDK4 and others as indicated.

The end-of-treatment assessment was conducted as follows. The planned treatment period was 24 weeks (8 cycles). Patients were treated in the absence of progressive disease or unacceptable treatment-associated toxicities. All patients who received at least one dose of the study drug and discontinued treatment for any reason (except death) had the end of treatment assessment performed. The assessment occurred up to 28 days following the last administration of 17-AAG and included a physical examination, with body weight and vital signs measurements, documentation of KPS Performance Status, hematology, coagulation and chemistry/electrolyte determinations, urinalysis, assessment of the patient's current medications and ongoing clinical adverse events (if any). Tumor assessments (myeloma laboratory tests, assessment of extramedullary disease, BMA, and other radiographic staging, if appropriate) were done at this time only if the previous assessment occurred more than 4 weeks prior to withdrawal.

The dose and schedule of administration of 17-AAG in the trial were as follows. 17-AAG was administered intravenously twice weekly for 2 weeks (on Day 1, 4, 8 and 11) every 3 weeks at escalating doses (calculated mg/m$^2$) infused over 60 minutes after pre-medication. For patients with a body surface area greater than 2.4 m$^2$, dosing was calculated using a maximum BSA of 2.4 m$^2$.

The preparation and administration of 17-AAG was as follows. 17-AAG was dissolved in 30% propylene glycol, 20% Cremophor® EL, and 50% ethanol to a concentration of 10 mg/mL in the vial. Drug product was available in 20 mL type 1 clear glass vials with a 20 mm finish (containing 200 mg/vial). The vials were closed with gray 20 mm Teflon coated serum stoppers and white 20 mm flip-off white lacquered flip tops. It was diluted 1:7 prior to administration with sterile WFI, USP (one part undiluted drug product to 6 parts sterile WFI). Dilution was performed under controlled, aseptic conditions. Final diluted drug product had a concentration of approximately 1.43 mg/mL. 17-AAG was prepared either using glass vacuum containers or compatible non-PVC, non-DEHP (di(2-ethylhexyl)-phthalate) IV admixture bags. Both systems require non-PVC, non-DEHP containing administration sets and either an in-line 0.22 µm filter or use of an extension set containing such a filter. Due to the light sensitivity of 17-AAG, protection from light is advised.

Depending on the body surface area and the assigned dose for individual patients, the dose of 17-AAG required different volumes of drug product to be added to the admixture bag. An overfill was calculated to account for any loss in the administration set.

As noted above, 17-AAG was administered intravenously over 60 minutes twice weekly for 2 weeks out of every 3 weeks. The total dose delivered was rounded to the nearest milligram.

All patients were pre-medicated prior to each infusion of 17-AAG. An appropriate pre-medication regimen was used for each patient based upon past history of potential Cremophor®-induced hypersensitivity reactions and the type and severity of the hypersensitivity reaction observed following treatment with 17-AAG. The standard pre-medication regimen was to pre-medicate with loratidine 10 mg p.o., famotidine 20 mg p.o., and either methylprednisolone 40-80 mg IV or dexamethasone 10-20 mg IV 30 minutes prior to infusion of 17-AAG. Choice of antihistamine and corticosteroid, route of administration, doses prior to 17-AAG infusion was at the investigator's discretion, but was similar to prophylaxis for other Cremophor®-containing products (such as Taxol® (paclitaxel)). Doses of corticosteroid were lowered if the patient was receiving concomitant prednisone. The high dose pre-medication regimen was to pre-medicate with diphenhydramine 50 mg IV, famotidine 20 mg IV and either methylprednisolone 80 mg IV or dexamethasone 20 mg IV, at least 30 minutes prior to the infusion of 17-AAG.

The doses and schedule of study drug were as follows. The initial patient cohort received the intravenous infusion of 17-AAG at a unit dose of 150 mg/m$^2$. Subsequent patient cohorts were enrolled per the escalation scheme outlined in the table below, as supported by observed toxicities. The subsequent cohorts received the following dosages: 220 mg/m$^2$, 275 mg/m$^2$, and 340 mg/m$^2$. with dose escalation to occur if <1 out of 6 evaluable patients has DLT at the 340 mg/m$^2$ dose level. Three patients were assigned to each cohort. If no DLT was observed in a cohort of three patients evaluable for dose escalating decision ("evaluable" is defined here as having received four treatments in a 3-week period and not having been withdrawn due to drug-related toxicity), then the next dose level was evaluated. If one of three evaluable patients experienced a DLT, then the cohort was increased to six evaluable patients. If two or more of six evaluable patients in a cohort experienced a DLT, then the MTD was deemed to have been exceeded; all further accrual was at the previous dose level. If no more than one of the six patients experienced a DLT, then the next dose level was evaluated. Once the MTD was defined, an additional number of patients was enrolled to arrive at a cumulative total of 12 patients at the MTD dose level.

Twenty-two patients were treated in accordance with this protocol. The patients had a median KPS of 90. 17-AAG was administered over approximately 1.0 hour. Of these 22 patients, currently 19 are evaluable.

Four patients were administered the 150 mg/m$^2$ dose (one hour intravenous infusion) twice weekly for every 2 out of 3 weeks. Of these four patients, all four are evaluable. One showed a MR (at least 25% reduction of serum M-protein). DLT was not observed in any of these four patients.

Nine patients were administered the 220 mg/m$^2$ dose (one hour intravenous infusion) twice weekly for every 2 out of 3 weeks. Of these nine patients, seven are currently evaluable. Of these seven evaluable patients, four are stable disease and three are progressive disease. DLT was observed in one patient; the DLT was liver infiltration of plasma cells with a Grade 3 elevated ALT. DLT was not observed in the other six patients. Analysis of BMAs of patients showed increased apoptosis (as determined by measuring mitochondrial potential) and decreased Akt comparing the data for that obtained at screening and Day 11 (p=0.06). Peripheral blood leukocytes (PBL) showed reactive induction of Hsp70 following treatment with 17-AAG.

Three patients were administered the 275 mg/m$^2$ dose (one hour intravenous infusion) twice weekly for every 2 out of 3 weeks. Of these three patients, all three are evaluable. DLT was not observed in any of these three patients.

Six patients were administered the 340 mg/m$^2$ dose (one hour intravenous infusion) twice weekly for every 2 out of 3 weeks. Of these six patients, five are evaluable.

Other than the single patient with a Grade 3 elevated ALT, the only drug-related toxicities observed in the patients were Grade 1-2 elevated transaminases, nausea, fatigue, diarrhea, anemia, myalgias and rash. No contraindication to Cremophor®-containing drugs was observed.

Of the above patients, 19 evaluable patients have been evaluated for antimyeloma activity. Of these 19 patients, there is one patient with a MR, eleven patients with stable disease after three or more cycles of treatment. One patient was considered a PR (90% reduction of urine M-protein) but was withdrawn from the study for skin rash and wheezing. The percent of patients with response (MR) is 5%, and the percent of patients with stable disease is 58%. Of the four patients dosed at 150 mg/m$^2$, one patient had a MR, two had stable disease and one had progressive disease. Of the seven patients dosed at 220 mg/m² four patients had stable disease and three had progressive disease. Of the three patients dosed at 275 mg/m², all three had stable disease. Of the five patients dosed at 340 mg/m², two patients had stable disease and three had progressive disease.

Figure 1:
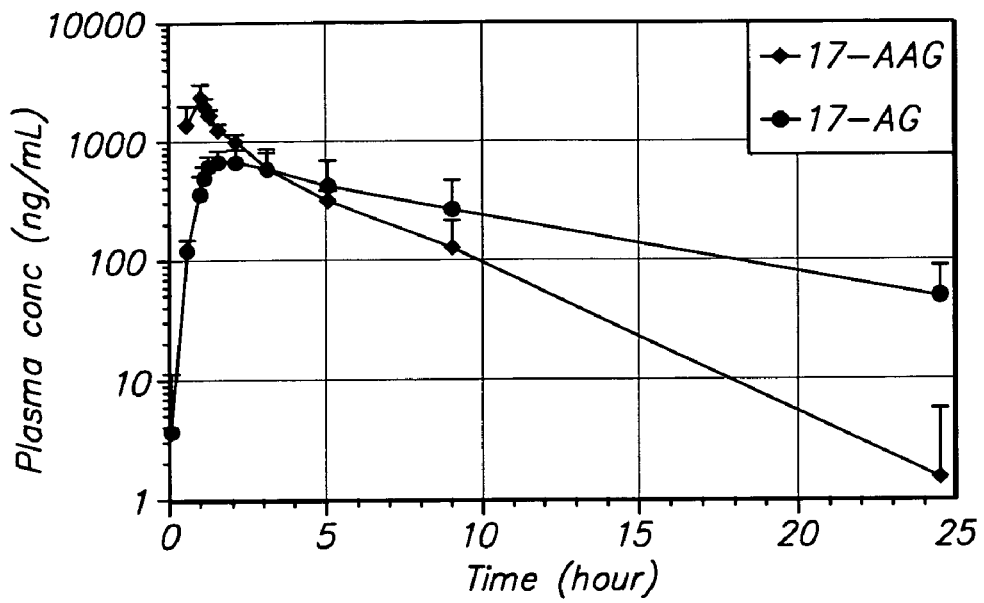
FIG. 1 shows the plasma concentration of 17-AAG and 17-AG versus actual time for a dose level of 150 mg/m$^2$ of 17-AAG (combined mean and standard deviation (SD) for Days 1 and 11).
Figure 2:
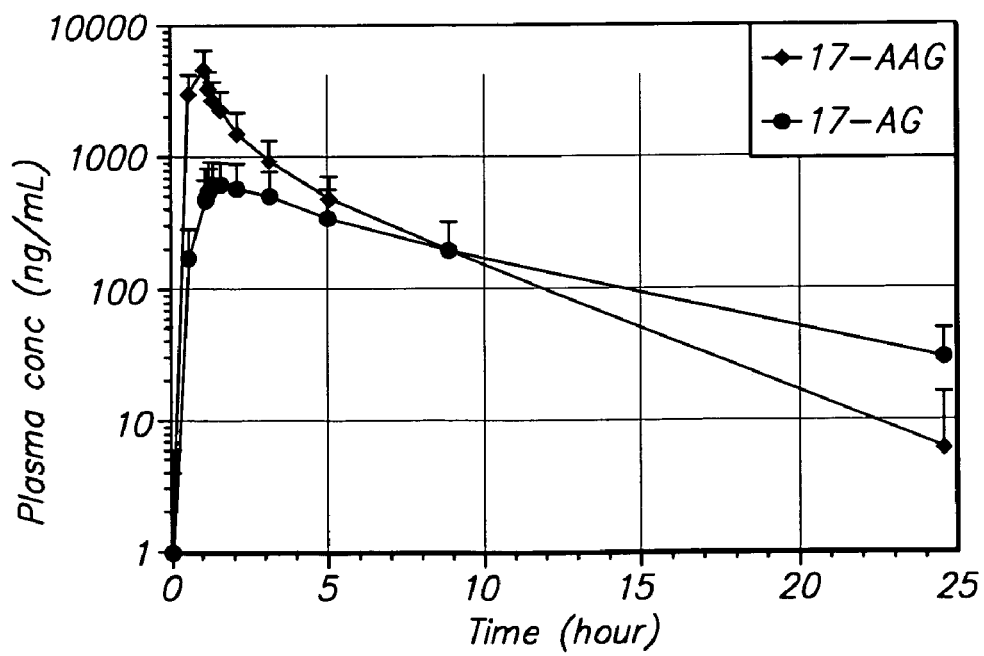
FIG. 2 shows the plasma concentration of 17-AAG and 17-AG versus actual time for a dose level of 220 mg/m$^2$ of 17-AAG (combined mean and SD for Days 1 and 11).
Figure 3:
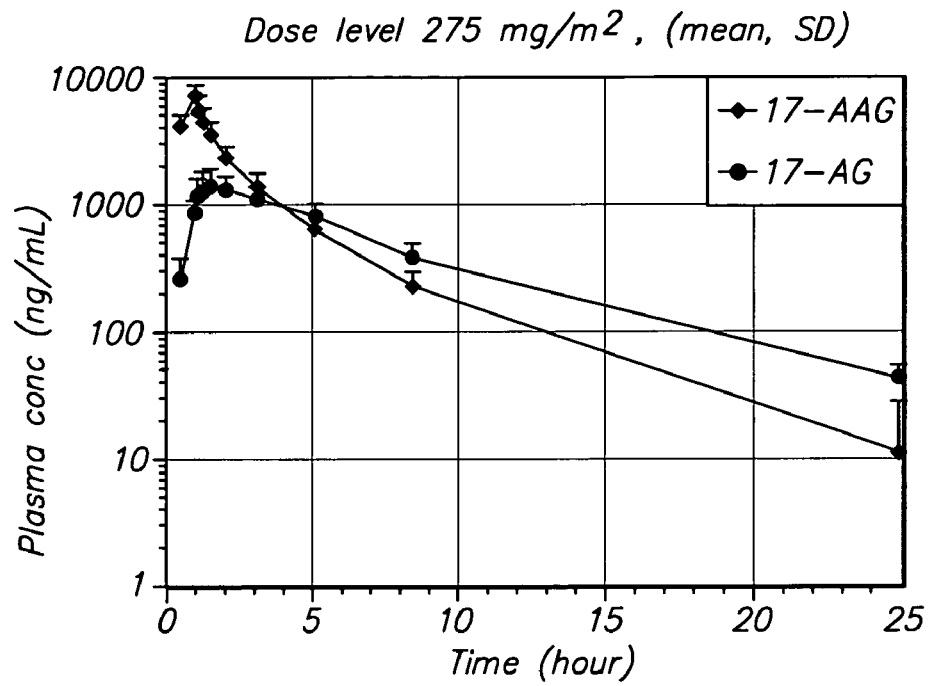
FIG. 3 shows the plasma concentration of 17-AAG and 17-AG versus actual time for a dose level of 275 mg/m$^2$ of 17-AAG (combined mean and SD for Days 1 and 11).
Figure 4:
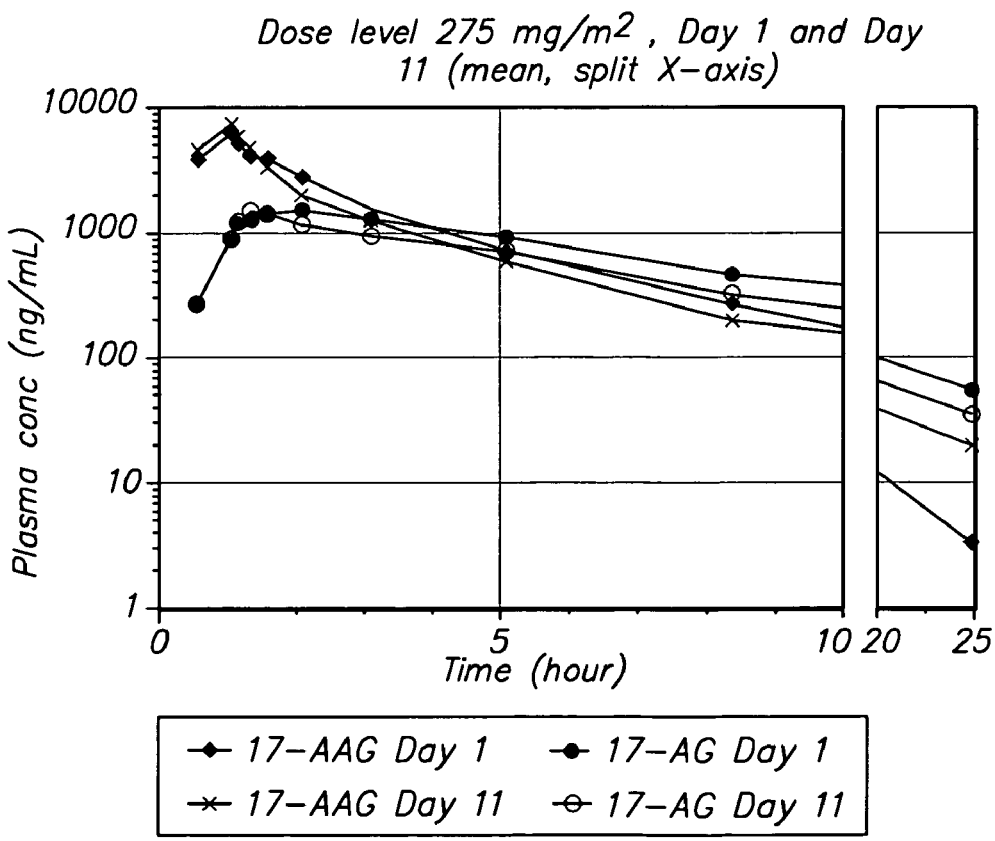
FIG. 4 shows the plasma concentration of 17-AAG for Day 1 and Day 11 and 17-AG for Day 1 and Day 11 versus actual time for a dose level of 275 mg/m$^2$ of 17-AAG (Day 1 and Day 11 (mean)).
Figure 5:
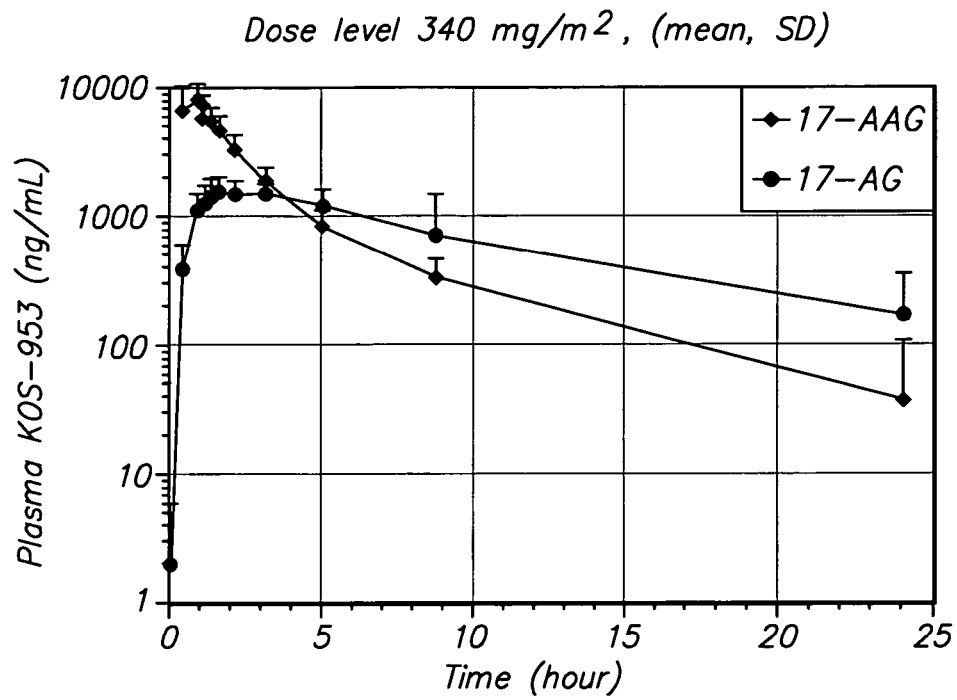
FIG. 5 shows the plasma concentration of 17-AAG and 17-AG versus actual time for a dose level of 340 mg/m$^2$ of 17-AAG (combined mean and SD for Days 1 and 11).

The PK analysis was performed as follows. Blood was collected as follows for plasma drug concentration analysis: pre-dose, 30 mins intra-infusion, just before the end-of-infusion (EOI), and 5, 15, 30 minutes and 1, 2, 4, 8 and 24 hours post infusion. FIGS. 1-3, and 5 plot the plasma concentration of 17-AAG and a major metabolite, 17-amino geldanamycin (17-AG), versus actual time by dose cohort. FIG. 4 shows the Day 1 and the Day 11 mean curves for parent drug and metabolite for dose cohort 275 mg/m².

The plasma concentration vs. time curves for parent drug 17-AAG and the major metabolite (17-AG) demonstrated very similar decay for Day 1, after the first infusion and Day 11, and after the fourth infusion of 17-AAG (FIG. 4). Inter-patient standard deviations were small.

Plasma concentration vs. time curves for 17-AG peaked ($C_{max}$) approximately half an hour after the $C_{max}$ for 17-AAG and the plasma level of 17-AG exceeded the parent drug from approximately 3 hours post infusion for the 150 and 275 mg/m² cohorts and approximately 7 hours post infusion for the 220 mg/m² cohort. The $C_{max}$ of 17-AAG increased in an approximately dose proportional manner. However, the $C_{max}$ of the 17-AG metabolite did not increased in a dose proporslower clearance for 17-AAG than average (CL=16.8 and CL=17.3 L/h/m² compared to the average for the cohort CL=25.3±9.6 L/h/m²).

PK parameters were calculated on plasma concentration time data by non-compartmental analysis using Kinetica version 4.3 software (Innaphase, Champs sur Marne, France). AUC was calculated by the mixed log-linear rule: the linear rule was applied to the range where concentration was ascending and the log-linear rule was applied to the range where the concentration was descending. $AUC_{last}$ is the area from t=0 to $t_{last}$, the last sampling time. $AUC_{extra}$ is the extrapolated area from $AUC_{last}$ to infinity and $AUC_{total}=AUC_{last}+AUC_{extra}$ and is also named $AUC_{0-\infty}$ area under the concentration-time curve from time zero to infinity. The terminal rate constant λz was calculated on at least three points on the elimination curve with values greater than the lower limit of quantitation. Table 4 lists the PK parameters for 17-AAG (mean±one standard deviation). Table 5 lists the areas, $C_{max}$, and half-life for the metabolite 17-AG (mean±one standard deviation). Across all patients, the half-life for 17-AAG ranged from 2.19±0.58 hours to 3.68±0.27 hours. Across all patients, the half-life for 17-AG ranged from 4.6±0.50 hours to 5.40±1.39 hours. There was no dose dependency for half-life, clearance or distributive volumes for these dose administrations. Total systemic clearance for 17-AAG ranged from 38.18±11.10 L/h to 54.92±6.76 L/h. The distributive volume ($V_z$) for 17-AAG ranged from 159.6±54.4 L to 204.2±65.6 L. The distributive volume ($V_{ss}$) for 17-AAG ranged from 123.4±23.4 L to 170.9±41.7 L.

TABLE 4

PK Parameters for 17-AAG

| PK Parameter | Dose (mg/m²) | | | |
|---|---|---|---|---|
| | 150 | 220 | 275 | 340 |
| $C_{max}$ (ng/mL) | 2,403 ± 605 | 4,671 ± 1,449 | 6,820 ± 1,715 | 9,355 ± 2,678 |
| $AUC_{last}$ (ng/ml * h) | 5,304 ± 757 | 9,162 ± 2,778 | 13,411 ± 1,482 | 18,653 ± 4,020 |
| $AUC_{total}$ (ng/mL * h) | 5,592 ± 757 | 9,460 ± 3,788 | 13,803 ± 1,540 | 18,997 ± 4,195 |
| Terminal $T_{1/2}$ (h) | 2.19 ± 0.58 | 2.68 ± 0.99 | 2.96 ± 1.34 | 3.30 ± 0.83 |
| Clearance (L/h) | 54.92 ± 6.76 | 46.77 ± 14.66 | 39.63 ± 8.92 | 35.71 ± 9.08 |
| $V_z$ (L) | 169.9 ± 30.3 | 171.0 ± 67.1 | 159.6 ± 54.4 | 174.0 ± 71.2 |
| $V_{ss}$ (L) | 170.9 ± 41.7 | 139.1 ± 45.7 | 123.4 ± 23.4 | 101.3 ± 27.7 |

TABLE 5

PK Parameters for 17-AG

| PK Parameter | Dose (mg/m²) | | | |
|---|---|---|---|---|
| | 150 | 220 | 275 | 340 |
| $C_{max}$ (ng/mL) | 725 ± 191 | 689 ± 265 | 1,493 ± 426 | 1,644 ± 440 |
| $AUC_{last}$ (ng/ml * h) | 5,232 ± 3,489 | 5,351 + 2,485 | 9,335 ± 2,400 | 12,613 ± 5,369 |
| $AUC_{total}$ (ng/mL * h) | 5,787 ± 3,785 | 4,645 ± 2,585 | 9,636 ± 2,400 | 13,121 ± 5,658 |
| Terminal $T_{1/2}$ (h) | 5.40 ± 1.39 | 5.25 ± 1.01 | 4.76 ± 0.34 | 4.70 ± 0.50 | tional manner. The $C_{max}$ of 17-AAG apparently goes up with increasing doses of 17-AAG but this is not necessarily true for the $C_{max}$ of 17-AG. This is true for the 275 and 340 mg/m² doses. (See FIG. 7.)

Figure 6:
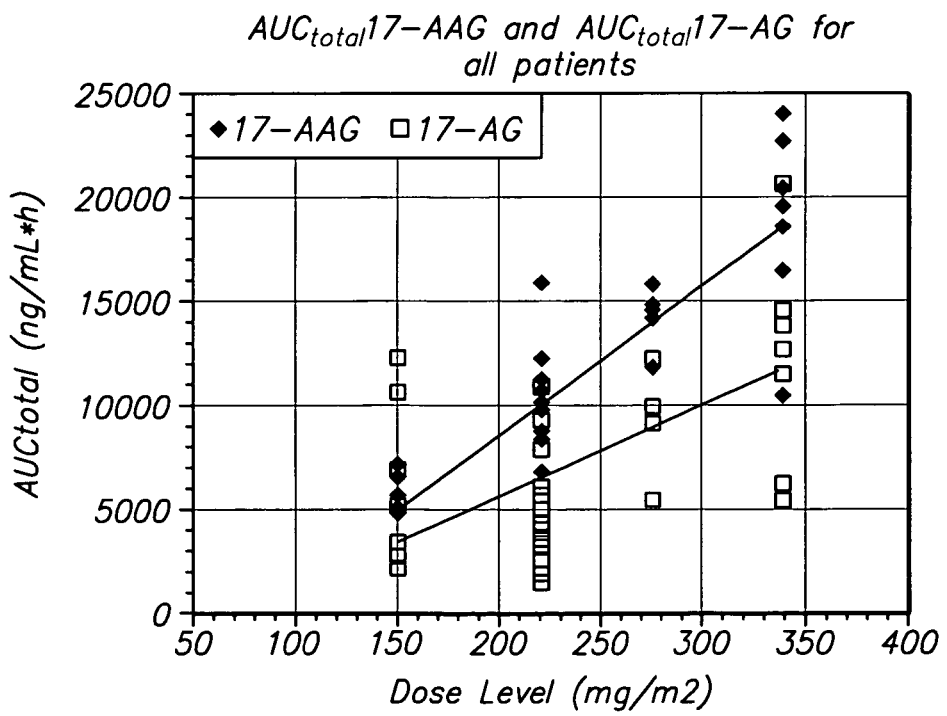
FIG. 6 shows the AUC$_{total}$ for 17-AAG and 17-AG for all patients.

The pattern of elimination did not change from Day 1 to Day 11 as demonstrated by all three patients on dose level 275 mg/m² (FIG. 4). None of them showed non-zero pre-dose plasma levels on Day 11. However, for dose level 220 mg/m², there was metabolite concentration in the trough levels on Day 11 for 2 out of the 10 patients. Both of these patients had $AUC_{total}$ increased with dose for 17-AAG, for the metabolite both the average $AUC_{total}$ and the average $C_{max}$ levels were lower than would be expected for a linear dose response for the 220 mg/m² cohort. In these 17 patients, there was no increase in $AUC_{total}$ between Day 1 and Day 11 for 17-AAG. For the metabolite (17-AG), the results were similar with no pattern of increase or decrease (FIG. 6). However, for two patients on 150 mg/m², the $AUC_{total}$ for metabolite exceeded the $AUC_{total}$ parent drug.

Between patients, the ratio of the metabolite to parent drug varied widely, from 31% to 173%. From Day 1 to Day 11 the ratio was similar for any specific patient sometimes slightly higher and for other patients slightly lower. Consequently, although the interpatient ratio differs greatly, each patient metabolizes the drug in a unique manner which does not change with subsequent doses.

This trial employed a formulation of 17-AAG in a Cremophor® base (cf. the DMSO/egg phospholipid formulation used in a previous trial (Banerji et al. 2002)). FIG. 7 superimposes the mean $C_{max}$ of 17-AAG and 17-AG for the results of this trial onto the results of that previous trial. FIG. 8 does the same for $AUC_{total}$ of 17-AAG.

Results for 17-AAG indicate that there is no difference in the $C_{max}$ or the $AUC_{total}$ for the two formulations. The very wide variation in $AUC_{total}$ for the 320 mg/m$^2$ dose level in Banerji et al. (2002) was not seen in either the 275 mg/m$^2$ or 340 mg/m$^2$ dose levels for the present study. The volume of infusates for the Cremophor® product for the 340 mg/m$^2$ was about 428 cc delivered in over 1 hour. The volume of infusate for the egg phospholipid/DMSO product for the 320 mg/m$^2$ was about 576 cc delivered in over 1 hour. Although the results for the first few patients may appear to give a lower $C_{max}$ for the metabolite than found in the previous study using the DMSO/egg phospholipid formulation, there are too few patients to ensure statistical significance.

The half-life ($T_{1/2}$) for 17-AAG and for 17-AG was similar to other studies and the CL=47.52±12.81 L/h and $V_{ss}$=144.45±43.51 L results were very close to the values reported in a previous study for treating various solid tumors for the weekly dosing schedule (Banerji et al. 2002; 17-AAG CL=33–71 L/h, $V_{ss}$=130±50 L and $t_{1/2}$=2.98±1.0 hours).

PD analysis was performed and indicated the following. The PD data for the 150 mg/m$^2$ and 220 mg/m$^2$ doses indicate that BMAs obtained prior to administration of 17-AAG and at Day 11 have an increase in apoptosis and a decrease in pAKT. BMAs were obtained from patients pre-study (prior to administration of 17-AAG) and on Day 11. MM cells were purified by a Fluorescence Activated Cell Sorter (FACS) from the BMA based upon CD138 expression. These CD138$^+$ cells collected were then tested for abnormal mitochondrial potential by measuring mitochondrial potential in plasma cells using Annexin V (BD Biosciences, San Jose, Calif.). FIG. 9 shows the percent of apoptosis of CD138$^+$ myeloma cells from samples from patients prior to administering 17-AAG and on Day 11. Abnormal mitochondrial potential is observed prior to apoptosis of that cell (programmed cell death). The statistical significance of the increased apoptosis has a p-value of 0.06. The percent of CD 128$^+$ cells with abnormal mitochondrial potential in BM increased from less than 5% (prior to treatment) to more than 40% (in Day 11 of treatment). The percent change increased by more than 35%. The percent change increased by more than eight-fold.

BMAs collected also showed decreased phosporylated AKT and pAKT when comparing samples from patients prior to administering 17-AAG and on Day 11 (see FIG. 10). FIG. 10 shows the percent of cells that have AKT detected over the total number of BM cells. AKT is a signalling protein that is upregulated in myeloma cells on the Ras/Raf/MAPK intracellular pathway critical to myeloma cell growth and progression. The statistical significance of the decrease in AKT$^+$ cells has a p-value of 0.057. The percent of AKT$^+$ cells over total BM cells decreased from more than 20% (prior to treatment) to less than 10% (in Day 11 of treatment). The percent change decreased by more than 10%. The percent change decreased by more than one half.

Figure 11B:
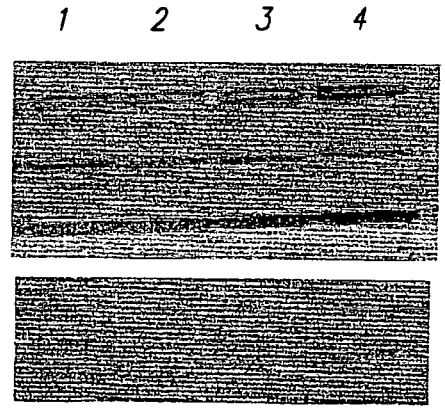

PBL obtained from patients prior to and four hours following the infusions of 17-AAG on Day 1 and Day 11 were run on a protein gel and immunobloted for Hsp70, total AKT, ILK, raf-1 and LCK. FIG. 10 shows the results for two patients (one dosed at 275 mg/m$^2$, and the other at 340 mg/m$^2$). The results for both of these patients showed an increase of Hsp70 (see FIG. 11), the typical heat stress response seen with HSP90 inhibitors.

The measurement of serum M-spike and urine M-protein in a patient treated at the 150 mg/m$^2$ dose level showed a 41% reduction of urine M-protein after two cycles of treatment (FIG. 12). The patient is considered to have a MR. The patient had the following regimens prior to enrolling in this study (and the respective results from these prior treatments): VAD (unknown response), bortezomib (progressive disease), bortezomib/dexamethasone (stable disease), lenalidomide (progressive disease), and autologous transplant.

The measurement of serum M-spike and IgG in a patient treated at the 275 mg/m$^2$ dose level showed a 11% reduction of serum M-spike after eight cycles of treatment (see FIG. 13). The patient is considered to have a stable disease three months, without any treatment, after completing the eight cycles of treatment. The patient had the following regimens prior to enrolling in this study (and the respective results from these prior treatments): thalidomide/dexamethasone (PR), thalidomide/dexamethasone/cyclophosphamide (PR), bortezomib (PR), and dexamethasone (progressive disease).

Although the present invention has been described in detail with reference to specific embodiments, those of skill in the art will recognize that modifications and improvements are within the scope and spirit of the invention. Citation of publications and patent documents is not intended as an admission that any such document is pertinent prior art, nor does it constitute any admission as to the contents or date of the same. The invention having now been described by way of written description, those of skill in the art will recognize that the invention can be practiced in a variety of embodiments and that the foregoing description are for purposes of illustration and not limitation of the following claims.

REFERENCES

Adams et al. (2005), WO 2005/063714.
Bagatell et al. (2001) Clin. Cancer. Res. 7:2076-2084, "Destabilization of Steroid Receptors by Heat Shock Protein 90-binding Drugs: A Ligand-independent Approach to Hormonal Therapy of Breast Cancer."
Bagchi et al. (1997) U.S. Pat. No. 5,662,883.
Banerji et al. (2002) Proc. 93rd Annu. Meet. Am. Assoc. Cancer Res. Abstract 1352, "A pharmacokineticaly (PK)-pharmacodynamically (PD) driven Phase I trial of the HSP90 molecular chaperone inhibitor 17-allylamin-17-demethoxygeldanamycin (17AAG)."
Banerji et al. (2005) J. Clin. Oncol. 23(1):4152-4161, "Phase I Pharmacokinetic and Pharmacodynamic Study of 17-Allylamino, 17-Demethoxygeldanamycin in Patients with Advanced Malignancies."
Bladé et al. (1998) Br. J Haematol. 102(5):1115-23, "Criteria for Evaluating Disease Response and Progression in Patients with Multiple Myeloma Treated by High-dose Therapy and Haemopoietic Stem Cell Transplantation."
Boni et al. (1997) U.S. Pat. No. 5,683,715.
Bosch et al. (1996) U.S. Pat. No. 5,510,118.
Burger et al. (2004) Anti-Cancer Drugs 15 (4):377-387, "17-(Allylamino)-17-demethoxygeldanamycin activity in human melanoma models."

Chen et al. (2005) Cancer Chemother. Pharmacol. 55:237-243, "Population pharmacokinetic analysis of 17-(allylamino)-17-demethoxygeldanamycin (17AAG) in adult patients with advanced malignancies."

Davies et al. (2003) Blood. 102(13):4504-11, "Insights into the multistep transformation of MGUS to myeloma using microarray expression analysis."

De Castro (1996) U.S. Pat. No. 5,534,270.

Desai et al. (2006) WO 2006/034147 A2.

Egorin et al. (1998) Cancer Res. 58:2385-2396, "Metabolism of 17-(allylamino)-17-demethoxygeldanamycin (NSC 330507) by murine and human hepatic preparations."

Goetz et al. (2005) J. Clin. Oncol. 23(6):1078-1087, "Phase I trial of 17-allylamino-17-demethoxygeldanamycin in patients with advanced cancer."

Grem et al. (2005), J. Clin. Oncol. 23(9):1885-93, "Phase I and pharmacologic study of 17-(allylamino)-17-demethoxygeldanamycin in adult patients with solid tumors."

Hostein et al. (2001) Cancer Res. 61:4003-4009, "Inhibition of Signal Transduction by the Hsp90 Inhibitor 17-Allylamino-17-demethoxygeldanamycin Results in Cytostasis and Apoptosis"

Isaacs et al. (2006) PCT application no. PCT/US2006/007210.

Jiang and Shapiro. (2002) Proc. 93rd Ann. Meet. Am Assoc. Cancer Res. Abstract 1645, "17-AAG induces Rb-dependent G1 arrest in lung cancer cell lines."

Lambert et al. (2000) WO 00/71163.

Mansfield et al. (2006) US 2006/0067953 A1.

Mitsiades et al. (2002) Oncogene 21, 5673-83, "Activation of NF-kappaB and upregulation of intracellular anti-apoptotic proteins via the IGF-1/Akt signaling in human multiple myeloma cells: therapeutic implications."

Mitsiades et al. (2006) Blood 107 (3), 1092-1100, "Antimyeloma activity of heat shock protein-90 inhibition"

Munster et al. (2001) Proc. Am. Soc. Clin. Oncol. 20:Abstract 327, "Phase I Trial of 17-(allylamino)-17-Demethoxygeldanamycin (17-AAG) in Patients (Pts) with Advanced Solid Malignancies."

National Cancer Institute (2003) Common Terminology Criteria for Adverse Events v3.0 (CTCAE).

Nguyen et al. (2000) Ann. Thorac. Surg. 70:1853-1860, "Modulation of metastasis phenotypes of non-small cell lung cancer cells by 17-allylamino 17-demethoxy geldanamycin."

Nimmanapalli et al. (2001) Cancer Res. 61:1799-1804, "Geldanamycin and Its Analogue 17-Allylamino-17-demethoxygeldanamycin Lowers Bcr-Abl Levels and Induces Apoptosis and Differentiation of Bcr-Abl-positive Human Leukemic Blasts."

Quay et al. (1998), WO 98/30205.

Rahman et al. (1995) U.S. Pat. No. 5,424,073.

Sasaki et al. (1979), J. Antibiotics 32 (8), 849-851, "Growth inhibition of virus transformed cells in vitro and antitumor activity in vivo of geldanamycin and its derivatives."

Sasaki et al. (1981), U.S. Pat. No. 4,261,989.

Schnur (1995), U.S. Pat. No. 5,387,584.

Schnur et al. (1999), U.S. Pat. No. 5,932,566.

Schulte and Neckers. (1998) Cancer Chemother. Pharmacol. 42:273-279, "The benzoquinone ansamycin 17-allylamino-17-demethoxygeldanamycin binds to HSP90 and shares important biologic activities with geldanamycin."

Sonntag et al. (2001) WO 01/10412 A1.

Straubinger et al. (1995) U.S. Pat. No. 5,415,869.

Tabibi et al. (2004) U.S. Pat. No. 6,682,758 B1.

Ulm et al. (2003) WO 03/086381 A1.

Ulm et al. (2004) WO 2004/082676 A1.

Wermuth (2003), "Designing Prodrugs and Bioprecursors," in Wermuth, ed., The Practice of Medicinal Chemistry, 2nd Ed., pp. 561-586 (Academic Press 2003).

Zhong et al. (2005) US 2005/0256097 A1.

What is claimed is:

1. A method of treating multiple myeloma (MM) in a subject in need of such treatment, comprising the step of administering to said subject a pharmaceutical formulation comprising a therapeutically effective dose of 17-allylamino-17-demethoxygeldanamycin (17-AAG) or 17-aminogeldanamycin (17-AG), and optionally a pharmaceutically acceptable carrier or diluent, and optionally repeating said administering step until no further therapeutic benefit is obtained, wherein said therapeutically effective dose is in the range of about 275 to about 420 mg/m$^2$ of 17-AAG, or an equivalent amount of 17-AG and results in an AUC$_{total}$ of 17-AAG per dose in the range of about 12,500 to about 20,000 ng/mL*h and/or an AUC$_{total}$ of 17-AG per dose in the range of about 5,000 ng/mL*h to about 18,000 ng/mL*h.

2. A method of treating MM in a subject in need of such treatment, comprising the step of administering to said subject multiple doses of 17-AAG or 17-AG to said patient over a time period of at least 2 weeks, wherein each such dose is in the range of about 275 to about 420 mg/m$^2$ of 17-AAG, or an equivalent amount of 17-AG that results in an AUC$_{total}$ of 17-AAG per dose in the range of about 12,500 to about 20,000 ng/mL*h and/or an AUC$_{total}$ of 17-AG per dose in the range of about 5,000 ng/mL*h to about 18,000 ng/mL*h.

3. The method of claim 2, wherein each dose of 17-AAG is about 340 mg/m$^2$ or an equivalent amount of 17-AG.

4. The method of claim 2, wherein said dose is administered twice weekly for at least two weeks.

5. The method of claim 4, wherein said dose is administered twice weekly for at least two weeks in a three week period.

6. The method of claim 5, wherein multiple cycles of treatment are administered to the subject, wherein each cycle of treatment comprises of said dose administered twice weekly for at least two weeks in a three week period.

7. The method of claim 1, wherein said dose is administered at a rate and frequency such that the C$_{max}$ of 17-AAG does not exceed 15,000 ng/mL.

8. The method of claim 1, wherein said dose is administered at a rate and frequency such that the C$_{max}$ of 17-AAG is greater than 1,800 ng/mL.

9. The method of claim 8, wherein said dose is administered at a rate and frequency such that the C$_{max}$ of 17-AAG is greater than 3,000 ng/mL.

10. The method of claim 1, wherein said dose is administered at a rate and frequency such that the C$_{max}$ of 17-AAG is greater than 1,800 but does not exceed 15,000 ng/mL.

11. The method of claim 10, wherein said dose is administered at a rate and frequency such that the C$_{max}$ of 17-AAG is greater than 3,000 but does not exceed 15,000 ng/mL.

12. The method of claim 1, wherein said dose is administered at a rate and frequency such that the C$_{max}$ of 17-AG does not exceed 2,000 ng/mL.

13. The method of claim 1, wherein said dose is administered at a rate and frequency such that the C$_{max}$ of 17-AG is greater than 500 ng/mL.

14. The method of claim 13, wherein said dose is administered at a rate and frequency such that the C$_{max}$ of 17-AG is greater than 900 ng/mL.

15. The method of claim 1, wherein said dose is administered at a rate and frequency such that the C$_{max}$ of 17-AG is greater than 500 but does not exceed 2,000 ng/mL.

16. The method of claim 15, wherein said dose is administered at a rate and frequency such that the $C_{max}$ of 17-AG is greater than 900 ng/mL but does not exceed 2,000 ng/mL.

17. A method of treating MM in a subject in need of such treatment, comprising the step of administering to said subject a therapeutically effective dose of 17-AAG or 17-AG that results in a combined $AUC_{total}$ of 17-AAG and 17-AG per dose in the range of about 17,500 ng/mL*h to about 43,000 ng/mL*h, wherein said therapeutically effective dose is in the range of about 275 to about 420 mg/m$^2$ of 17-AAG or an equivalent amount of 17-AG.

18. The method of claim 17, wherein said dose is administered at a rate and frequency such that the $C_{max}$ of 17-AAG does not exceed 15,000 ng/mL or the $C_{max}$ of 17-AG does not exceed 2,000 ng/mL.

19. The method of claim 17, wherein said dose is administered at a rate and frequency such that the $C_{max}$ of 17-AAG is greater than 1,800 ng/mL or the $C_{max}$ of 17-AG is greater than 500 ng/mL.

20. The method of claim 19, wherein said dose is administered at a rate and frequency such that the $C_{max}$ of 17-AAG is greater than 3,000 ng/mL or the $C_{max}$ of 17-AG is greater than 900 ng/mL.

21. The method of claim 17, wherein said dose is administered at a rate and frequency such that the $C_{max}$ of 17-AAG is greater than 1,800 but does not exceed 15,000 ng/mL or the $C_{max}$ of 17-AG is greater than 500 but does not exceed 2,000 ng/mL.

22. The method of claim 21, wherein said dose is administered at a rate and frequency such that the $C_{max}$ of 17-AAG is greater than 3,000 but does not exceed 15,000 ng/mL or the $C_{max}$ of 17-AG is greater than 900 but does not exceed 2,000 ng/mL.

23. A method of treating MM in a subject in need of such treatment, comprising the step of administering to said subject a therapeutically effective dose of 17-AAG that results in a Terminal $T_{1/2}$ of 17-AAG in the range of 3 to 4.5 h, and wherein said therapeutically effective dose is in a range of between about 275 and about 420 mg/m$^2$ of 17-AAG, or an equivalent amount of 17-AG.

24. The method of claim 23, wherein said dose administered results in an $AUC_{total}$ of 17-AAG per dose in the range of about 12,500 ng/mL*h to about 25,000 ng/mL*h.

25. A method of treating MM in a subject in need of such treatment, comprising the step of administering to said subject a therapeutically effective dose of 17-AG that results in a Terminal $T_{1/2}$ of 17-AG in the range of 4 to 7 h, wherein said therapeutically effective dose is in the range of about 275 to about 420 mg/m$^2$ of 17-AG.

26. The method of claim 25, wherein said dose results in an $AUC_{total}$ of 17-AG per dose in the range of about 5,000 to about 18,000 ng/mL*h.

27. A method of treating MM in a subject in need of such treatment, comprising the step of administering to said subject a therapeutically effective dose of 17-AAG that results in a Volume of distribution $V_z$ of 17-AAG in the range of 100 to 270 L, wherein said therapeutically effective dose is in the range of about 275 to about 420 mg/m$^2$ of 17-AAG.

28. The method of claim 27, wherein said dose results in an $AUC_{total}$ of 17-AAG per dose in the range of about 12,500 to about 25,000 ng/mL*h.

29. A method of treating MM in a subject in need of such treatment, comprising the step of administering to said subject a therapeutically effective dose of 17-AAG that results in a Clearance of 17-AAG in the range of 30 to 50 L/h, wherein said therapeutically effective dose is in the range of about 275 to about 420 mg/m$^2$ of 17-AAG.

30. The method of claim 29, wherein said dose results in an $AUC_{total}$ of 17-AAG per dose in the range of about 12,500 to about 25,000 ng/mL*h.

31. A method of treating MM in a subject in need of such treatment, comprising the step of administering to said subject a therapeutically effective dose of 17-AAG that results in a Volume of distribution $V_{SS}$ of 17-AAG in the range of 100 to 150 L, wherein said therapeutically effective dose is in the range of about 275 to about 420 mg/m$^2$ of 17-AAG.

32. The method of claim 31, wherein said dose results in an $AUC_{total}$ of 17-AAG per dose in the range of about 12,500 to about 25,000 ng/mL*h.

33. The method of claim 1, wherein said administering step results in an induction of HSP70 in the peripheral blood mononuclear cells of said subject.

34. The method of claim 33, wherein said induction of HSP70 is observable one day after said administering step.

35. The method of claim 1, wherein said administering step results in an increase of apoptosis of CD 138$^+$ cells among the bone marrow aspirate cells of said subject.

36. The method of claim 35, wherein said increase of apoptosis of CD138$^+$ cells is observable four hours after said administering step.

37. The method of claim 1, wherein said administering step results in a decrease of total AKT in bone marrow aspirate cells of said subject.

38. The method of claim 37, wherein said decrease of total AKT is observable four hours after said administering step.

* * * * *